United States Patent [19]
Mendlein et al.

[11] Patent Number: 6,013,031
[45] Date of Patent: Jan. 11, 2000

[54] METHODS AND DEVICES FOR IMPROVING ULTRASONIC MEASUREMENTS USING ANATOMIC LANDMARKS AND SOFT TISSUE CORRECTION

[76] Inventors: John D. Mendlein, 680 Neptune Ave., Encinitas, Calif. 92024; Philipp Lang, 225 Lincoln Way #206, San Francisco, Calif. 94122

[21] Appl. No.: 09/036,940

[22] Filed: Mar. 9, 1998

[51] Int. Cl.$^7$ ..................................................... A61B 8/00
[52] U.S. Cl. ........................... 600/442; 600/443; 600/449
[58] Field of Search ................................. 600/449, 437, 600/442, 459; 73/597, 599

[56] References Cited

U.S. PATENT DOCUMENTS

| | | |
|---|---|---|
| 3,648,685 | 3/1972 | Hepp et al. . |
| 3,713,329 | 1/1973 | Munger . |
| 3,782,177 | 1/1974 | Hoop . |
| 3,847,141 | 11/1974 | Hoop . |

(List continued on next page.)

FOREIGN PATENT DOCUMENTS

WO 80/02796   6/1980   WIPO .

OTHER PUBLICATIONS

Agren, M., et al., Calc Tiss Int. vol. 48, pp. 240–244, 1991.
Biot, M. A., J Acoust Soc Am, vol.34, pp. 1254–1264, 1962.
Blake, G. M., et al., Br J Radiol, vol. 67, pp. 1206–1209, 1994.
Brooke–Wavell, K., et al., Calc Tissue Int, vol. 57, pp. 20–24, 1995.
Chappard, C., et al., Osteoporosis Int, vol. 7, pp. 316–322, 1997.
Dretakis, E., et al., Br J Radiol, vol. 67, pp. 636–638, 1994.
Evans, W.D., et al., Phys Med Biol, vol. 40, pp. 137–151, 1995.
Faulkner, K. G., et al., Am J Roentgenol, vol. 157, pp. 1229–1237, 1991.
Fournier, B., et al., Osteoporosis Int., vol. 7, pp. 363–369, 1997.
Gluer, C. C., et al., J Bone Min Res, vol. 7(9), pp. 1071–1079, 1992.
Gluer, C. C., et al., Calc Tiss Int, vol. 55, pp. 46–52, 1994.
Goss, S. A., et al., J. Acoust Soc Ann, vol. 64(2), pp. 423–457, 1978.
Greenspan, M., et al., J Acoust Soc Am, vol. 31, pp. 75–76, 1959.
Hans, D., et al., Bone, vol. 16, pp. 295–300, 1995.
Johnansen, A., et al., Osteoporosis International, vol. 7, pp. 44–47, 1997.
Jorgensen, H. L., et al., Bone, vol. 21, pp. 109–112, 1997.
Kotzki, P.O., et al., Calc Tiss Int, vol. 54, pp. 91–95, 1994.
Lang, P., et al., Radiol Clin North Am, vol. 29, pp. 49–76, 1991.
Langton, C. M., et al., Bone, vol. 18, 6, pp. 495–503, 1996.
Langton, C. M., et al., Eng Med, vol. 13, pp. 89–91, 1984.
Laugier, P., et al., Bone, vol. 20 (2), pp. 157–165, 1997.
Laugier, P., et al., Calc Tiss Int, vol. 58, pp. 326–331, 1966.
Langier, P., et al., Clinical Rheumatology, vol. 13 (Suppl. 1), pp. 22–32, 1994.

(List continued on next page.)

*Primary Examiner*—Marvin M. Lateef
*Assistant Examiner*—Ali M. Imam

[57] ABSTRACT

The invention provides for ultrasonic methods, compositions and devices. particularly methods, compositions and devices that provide for reproducible positioning of the ultrasonic transducer(s) over an anatomic region using anatomic landmarks. The invention provides for improved interrogation devices that reproducibly position transducer (s) over an interrogation site.

25 Claims, 19 Drawing Sheets

U.S. PATENT DOCUMENTS

| | | |
|---|---|---|
| 4,043,181 | 8/1977 | Nigam . |
| 4,048,986 | 9/1977 | Ott . |
| 4,056,970 | 11/1977 | Sollish . |
| 4,217,912 | 8/1980 | Hubmann et al. . |
| 4,224,829 | 9/1980 | Kawabuchi et al. . |
| 4,235,243 | 11/1980 | Saha . |
| 4,242,911 | 1/1981 | Martin . |
| 4,361,154 | 11/1982 | Pratt . |
| 4,383,533 | 5/1983 | Lovelace et al. . |
| 4,421,119 | 12/1983 | Pratt . |
| 4,446,737 | 5/1984 | Hottier . |
| 4,476,873 | 10/1984 | Sorenson . |
| 4,522,068 | 6/1985 | Smith . |
| 4,530,360 | 7/1985 | Duarte . |
| 4,658,827 | 4/1987 | He et al. . |
| 4,669,482 | 6/1987 | Ophir et al. .......................... 600/449 |
| 4,688,428 | 8/1987 | Nicolas . |
| 4,702,258 | 10/1987 | Nicolas et al. . |
| 4,774,959 | 10/1988 | Palmer et al. . |
| 4,830,015 | 5/1989 | Okazaki . |
| 4,913,157 | 4/1990 | Pratt et al. . |
| 4,930,511 | 6/1990 | Rossman et al. . |
| 5,042,489 | 8/1991 | Wiener et al. . |
| 5,054,490 | 10/1991 | Rossman et al. . |
| 5,099,849 | 3/1992 | Rossman et al. . |
| 5,119,820 | 6/1992 | Rossman et al. . |
| 5,218,963 | 6/1993 | Mazess . |
| 5,271,403 | 12/1993 | Paulos . |
| 5,343,863 | 9/1994 | Wiener et al. . |
| 5,349,959 | 9/1994 | Wiener et al. . |
| 5,452,722 | 9/1995 | Langton ................................ 600/449 |
| 5,483,965 | 1/1996 | Wiener et al. . |
| 5,547,459 | 8/1996 | Kaufman et al. . |
| 5,564,423 | 10/1996 | Mele et al. . |
| 5,603,325 | 2/1997 | Mazess et al. . |
| 5,649,538 | 7/1997 | Langton . |
| 5,651,363 | 7/1997 | Kaufman et al. . |
| 5,785,656 | 7/1998 | Chiabrera et al. . |
| 5,806,520 | 9/1998 | Berger et al. ......................... 600/442 |
| 5,810,737 | 9/1998 | Hamatsu et al. . |

OTHER PUBLICATIONS

Laugier, P., et al., Calc Tiss Int, vol. 54, pp. 83–86, 1994.

McCloskey, E. V., et al., Clin Sci, vol. 78, pp. 221–227, 1990.

Njeh, C. F., et al., Med Eng Phys, vol. 18, pp. 373–381, 1996.

Roux, C., et al., J Bone Min Res, vol. 11(8), pp. 1112–1118, 1996.

Turner, C.H., et al., Calc Tiss Int, vol. 49, pp. 116–119, 1991.

Williams, J. L., J Acoust Soc Am, vol. 91, pp. 1106–1112, 1992.

Zagzebski, J. A., et al., Calc Tiss Int, vol. 49, pp. 107–111, 1991.

METHODS AND DEVICES FOR IMPROVING ULTRASONIC MEASUREMENTS USING ANATOMIC LANDMARKS AND SOFT TISSUE CORRECTION

TECHNICAL FIELD

The invention relates to ultrasonic methods, compositions and devices. particularly methods, compositions and devices that provide for reproducible positioning of the ultrasonic transducer(s) over an anatomical region using anatomical landmarks.

BACKGROUND

Ultrasonic techniques have recently been introduced as methods free of ionizing radiation for non-invasive assessment of skeletal status in patients with osteoporosis. Quantitative aspects of these ultrasonic techniques can permit assessment of bone mass and density, as well as bone structure. Ultrasonic techniques for evaluating skeletal status also include measurements of speed of sound ("SOS") that reflect the transmission velocity of ultrasonic waves passing through bone tissue and soft tissue, measurements of broadband ultrasonic attenuation ("BUA") that assess the frequency dependence of ultrasonic attenuation, and pulse echo techniques that measure the energy scattered from the internal structure of the bone.

Many different measurement sites have been proposed for osteoporosis, such as the tibia, the patella, the phalanges, or the calcaneus. The calcaneus is preferred for quantitative ultrasonic measurements of skeletal status. It is composed of predominantly trabecular bone with only a thin cortical bone envelope medially and laterally which together provide an excellent medium for detecting changes in SOS and BUA measurements. The calcaneus also permits convenient ultrasonic interrogation for the operator and the patient alike.

Although a number of commercial devices exist for diagnosis of osteoporosis, clinicians have recognized the limitations of such devices and methods. Correlations between quantitative ultrasonic measurements and assessments of bone mineral density using quantitative computed tomography, dual x-ray absorptiometry, and single photon absorptiometry have been reported to be poor at the calcaneus, as well as at other sites.

Consequently, the inventors have recognized the need, among other things, to provide reliable ultrasonic devices and accurate, and qualitative or quantitative methods for ultrasonic measurements in the diagnosis of osteoporosis, as well as methods and devices to generally improve diagnostic tools based on ultrasonic measurements. The methods and devices provided herein permit, among other things, correction of ultrasonic parameters, such as speed of sound and broadband ultrasonic attenuation, for soft tissue interposed in the ultrasonic beam.

SUMMARY

While many of the embodiments of the invention will find particular application in clinical measurements, such as BUA or SOS, and surgical procedures, such trocar procedures and catheter procedures, the invention provides for general ultrasonic devices and methods that will be applicable to many clinical applications.

The invention provides for an improved ultrasonic system for tissue ultrasonic interrogation, comprising: a) a first ultrasonic transducer with an axis of transmission in common with a second ultrasonic transducer, wherein the axis of transmission is through a portion of tissue, b) an x, y positioner that engages the first ultrasonic transducer and the second ultrasonic transducer, the x, y positioner controllably positions the first ultrasonic transducer and the second ultrasonic transducer in a desired manner between at least a first and a second position while generally maintaining the axis of transmission, and c) a computational unit designed to manage ultrasonic signal transmission and reception of the first ultrasonic transducer and the second ultrasonic transducer in either A scan or B scan mode or both and may optionally be designed to control movement of the x, y positioner. The ultrasonic system can further comprise a z positioner that positions at least one of the first or second ultrasonic transducers, and the z positioner changes the distance of transmission along the axis of transmission between the first ultrasonic transducer and the second ultrasonic transducer. The ultrasonic system may include a computational unit that can identify an anatomic landmark in an interrogated tissue and direct the x, y positioner to a position over the anatomic landmark, and thereby positioning the first ultrasonic transducer and second ultrasonic transducer to have an axis of transmission generally through the anatomic landmark.

In another embodiment, the invention includes an ultrasonic system for automated ultrasonic identification of an anatomical landmark, comprising: a) an ultrasonic transducer unit comprising either 1) a first ultrasonic transducer that can transmit and receive signals or 2) a pair of ultrasonic transducers where a first member of the pair is designed to transmit signals and a second member of the pair is designed to receive signals, and b) a computational unit designed to manage ultrasonic signal transmission and reception of the ultrasonic transducer unit and to process signals to identify an anatomical landmark in an anatomical region in either a A scan or B scan mode or both. The ultrasonic system can further comprise a positioning unit for changing the spatial relationship between the anatomic landmark in the anatomical region and the ultrasonic transducer unit, thereby permitting interrogation with reference to the anatomic landmark in the anatomical region by positioning the transducer unit with respect to the anatomical landmark.

In another embodiment, the invention includes an ultrasonic method for generating an anatomic landmark for ultrasonic interrogation, comprising: positioning, with respect to an anatomical region, an ultrasonic transducer unit comprising either 1) a first ultrasonic transducer that can transmit and receive signals or 2) a pair of ultrasonic transducers where a first member of the pair is designed to transmit signals and a second member of the pair is designed to receive signals, interrogating the anatomical region with the ultrasonic transducer unit, identifying an anatomic landmark in the anatomical region with an ultrasonic property of the anatomical region, and storing the anatomic landmark in a storage device. The ultrasonic method may include the steps of comparing the location and axis of transmission of the ultrasonic transducer unit to the location of the anatomic landmark and positioning the ultrasonic transducer unit to produce an axis of transmission at a preselected or desired set of coordinates in relation to the anatomic landmark.

In another embodiment, the invention includes an ultrasonic method for generating an anatomic landmark for ultrasonic interrogation of an anatomical region, comprising: a) positioning, if necessary, on the surface of a patient, with respect to an anatomical region, an ultrasonic transducer unit comprising either 1) a first ultrasonic transducer that can transmit and receive signals or 2) a pair of ultrasonic transducers wherein a first member of the pair is designed to transmit signals and a second member of the pair is designed to receive signals, b) interrogating the anatomical region with the ultrasonic transducer unit at a first transmission angle, c) interrogating the anatomical region with the ultrasonic transducer unit at a second transmission angle, and d) identifying an anatomic landmark in common with the signals obtained in steps (b) and (c) in the anatomical region with an ultrasonic property of the anatomical region. The ultrasonic method may include the step of storing the anatomic landmark in a storage device. The positioning step may also include positioning the transducer unit at a plurality of predetermined transmission angles for interrogation. Typically, the use of a second transmission angle increases the accuracy of the anatomical landmark compared to interrogation with a single transmission angle.

In another embodiment, the invention includes a computer program product, comprising:

a) instructions for a positioning unit to position a transducer or plurality of transducers at a plurality of interrogation sites in an anatomical region, b) instructions for interrogating the anatomical region with the transducer or the plurality of transducers at the plurality of interrogation sites, c) instructions for generating a map of the anatomical region using ultrasonic measurements from the plurality of interrogation sites, d) instructions for the positioning unit to position the transducer or the plurality of transducers at a second plurality of interrogation sites in the anatomical region if the map lacks sufficient features to be clinically relevant for a clinically relevant measurement, e) instructions for interrogating the anatomical region for a clinically relevant measurement;

wherein instructions (a) through (e) permit the generation of the map which facilitates a clinically relevant measurement and instructions (a) through (e) are stored on a computer retrievable medium. The computer program product can also include instructions for comparing the map with a reference map of substantially the same anatomical region using predefined criteria, the predefined criteria optionally comprising percent similarity of contours of bones, percent similarity of an anatomical landmark or percent similarity of reflective surfaces; instructions for interrogating the anatomical region for a clinically relevant measurement if the map matches the reference map; and instructions for the positioning unit to position the transducer or the plurality of transducers at a second plurality of interrogation sites in the anatomical region if the map lacks sufficient features to be clinically relevant for a clinically relevant measurement.

Figure 1:
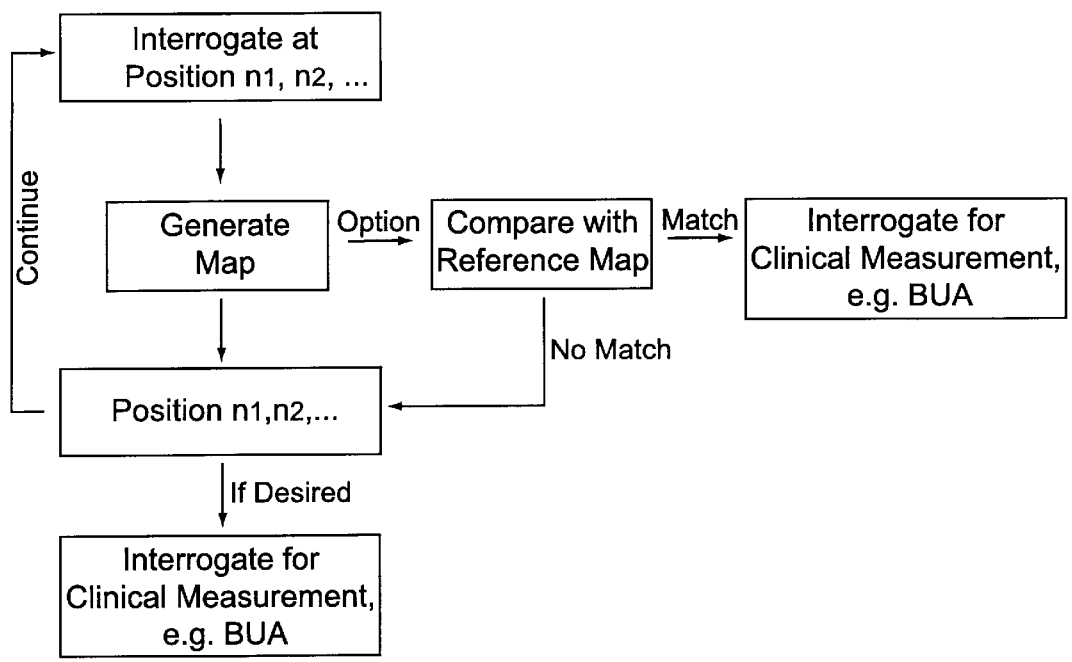
FIG. 1 shows one embodiment of the invention relating to methods of interrogating a tissue, generating an anatomical map or instructing a positioner to position a transducer(s). An anatomical map is generated from data by interrogating the tissue at a first transducer(s) position(s) ($n_1$), for instance using either A scan or B scan or both. A clinical measurement is then made at the first position $n_1$. The process of interrogation, map generation and clinical measurement can be repeated at each subsequent position ($n_1$, $n_2$, . . . ). Optionally, the anatomical map can be compared to a reference map that is usually stored in computational unit. When a suitable match occurs with the reference map interrogation can be initiated.

DETAILED DESCRIPTION OF THE INVENTION 1.0 Abbreviations and Definitions

ABBREVIATIONS include broadband ultrasonic attenuation (BUA) and speed of sound (SOS).

Acoustic communication refers to the passage of ultrasonic waves between two points in a predetermined manner. Usually, this is accomplished by selecting a desired pathway between the two points that permits the passage of ultrasonic waves either directly or indirectly. Direct passage of ultrasonic waves would occur, for instance, when an ultrasonic crystal is directly disposed to (usually touching) an acoustic coupling material, such as a composite. Indirect passage of ultrasonic waves would occur, for instance, when an ultrasonic crystal is located at a predetermined distance from an acoustic coupling material or when a number of acoustic coupling materials, often heterogenous materials, form two or more layers.

Acoustic coupler refers to a connection or plurality of connections between an ultrasonic crystal and a substance that reflects or passes ultrasonic pulses and is not part of the device or object being interrogated. The acoustic coupler will permit passage of ultrasonic waves. It is desirable for such couplers to minimize attenuation of ultrasonic pulses or signals and to minimize changes in the physical properties of an ultrasonic wave, such as wave amplitude, frequency, shape and wavelength. Typically, an ultrasonic coupler will either comprise a gel or other substantially soft material, such as a pliable polymer matrix, that can transmit ultrasonic pulses. Alternatively, an ultrasonic coupler can be a substantially solid material, such as a polymer matrix, that can transmit ultrasonic pulses. An ultrasonic coupler is usually selected based on its acoustic impedance match between the object being interrogated and the ultrasonic crystal(s). If a reflective surface is desired, for instance as a spatial marker, a larger impedance difference is selected compared to situations where it is advantageous to minimize a reflective surface to avoid a sharp reflective surface.

Acoustic coupling material is a material that passes ultrasonic waves, usually from a probe to a subject or tissue to be interrogated. It is usually not a living material and is most often a polymer or gel or acoustic coupler.

Acoustic mirror refers to a device that can reflect an ultrasonic wave and redirect the ultrasonic wave in a predetermined manner. If the original ultrasonic waves are transmitted at an angle $\alpha$, which is measured relative to the surface of the plane of the acoustic mirror, the reflected ultrasonic waves can be oriented at an angle $\alpha'=180°-\alpha$ relative to the plane of the acoustic mirror. An acoustic mirror(s) can be used in an ultrasonic system to vary the transmission angle.

Anatomical region refers to a site on the surface of the skin, tumor, organ or other definable biomass that can be identified by an anatomical feature(s) or location. Anatomical region can include the biomass underlying the surface. Usually, such a region will be definable according to standard medical reference methodology, such as that found in Williams et al., Gray's Anatomy, 1980.

BUA means broadband ultrasonic attenuation and when measured a BUA value is expressed as dB/MHz. Note that actual attenuation of broadband ultrasonic waves increases as soft tissue thickness increases, while BUA values (dB/MHz) decrease as soft tissue thickness increases. This distinction is often not recognized in the literature, which leads to misleading or potentially misleading conclusions about the effect of soft tissue on actual attenuation of broadband ultrasonic waves and BUA values.

A-scan refers to an ultrasonic technique where an ultrasonic source transmits an ultrasonic wave into an object, such as a patient's body, and the amplitude of the returning echoes (signals) are recorded as a function of time. Structures that lie along the direction of propagation are interrogated. As echoes return from interfaces within the object or tissue, the transducer crystal produces a voltage that is proportional to the echo intensity. The sequence of signal acquisition and processing of A-scan data in a modern ultrasonic instrument usually occurs in six major steps:

Detection of the echo (signal) occurs via mechanical deformation of the piezoelectric crystal and is converted to an electric signal having a small voltage.

Preamplification of the electronic signal from the crystal, into a more useful range of voltages is usually necessary to ensure appropriate signal processing.

Time Gain Compensation compensates for the attenuation of the ultrasonic signal with time, which arises from travel distance. Time gain compensation may be user-adjustable and may be changed to meet the needs of the specific application. Usually, the ideal time gain compensation curve corrects the signal for the depth of the reflective boundary. Time gain compensation works by increasing the amplification factor of the signal as a function of time after the ultrasonic pulse has been emitted. Thus, reflective boundaries having equal abilities to reflect ultrasonic waves will have equal ultrasonic signals, regardless of the depth of the boundary.

Compression of the time compensated signal can be accomplished using logarithmic amplification to reduce the large dynamic range (range of smallest to largest signals) of the echo amplitudes. Small signals are made larger and large signals are made smaller. This step provides a convenient scale for display of the amplitude variations on the limited gray scale range of a monitor.

Rectification, demodulation and envelope detection of the high frequency electronic signal permits the sampling and digitization of the echo amplitude free of variations induced by the sinusoidal nature of the waveform.

Rejection level adjustment sets the threshold of signal amplitudes that are permitted to enter a data storage, processing or display system. Rejection of lower signal amplitudes reduces noise levels from scattered ultrasonic signals.

B-scan refers to an ultrasonic technique where the amplitude of the detected returning echo is recorded as a function of the transmission time, the relative location of the detector in the probe and the signal amplitude. This is often represented by the brightness of a visual element, such as a pixel, in a two-dimensional image. The position of the pixel along the y-axis represents the depth, i.e. half the time for the echo to return to the transducer (for one half of the distance traveled). The position along the x-axis represents the location of the returning echoes relative to the long axis of the transducer, i.e. the location of the pixel either in a superoinferior or mediolateral direction or a combination of both. The display of multiple adjacent scan lines creates a composite two-dimensional image that portrays the general contour of internal organs.

Chip refers to any current and future electronic hardware device that can be used in a computational unit and can be used as an aid in controlling the components of an ultrasonic unit including: 1) timing and synchronizing trigger pulses and subsequent transmission of ultrasonic waves, 2) measuring and analyzing incoming ultrasonic signals, 3) comparing data to predetermined standards and data cut-offs (e.g. electronic filtering), and 4) performing multiple other simple and complex calculations. Typically, a chip is silicon-based, micro-electronic circuit.

Computational unit refers to any current or future hardware, software (e.g. computer program), chip or other device used for calculations or for providing instructions now developed or developed in the future. The computational unit may be used for controlling the ultrasonic generator or source, for defining or varying the firing rate and pulse repetition rate (as well as other parameters related to the ultrasonic generator or source), for measuring the reflected signal, for image reconstruction in B-scan mode and for filtering and thresholding of the ultrasonic signal. Other applications of the computational unit to the methods and devices described herein will be recognized by those skilled in the art. The computational unit may be used for any other application related to this technology that may be facilitated with use of computer software or hardware. The computational unit may comprise a computer program product with instructions to control the ultrasonic system. Such computer program products may be stored in storage devices, such as hard drives, floppy discs, electronic storage devices or any other storage device capable of reliable storage and retrieval of information (including electronic signals).

Crystal refers to the material used in the ultrasonic transducer to transmit ultrasonic waves and includes any current and future material used for this purpose. Crystals typically consist of lead zirconate titanate, barium lead titanate, lead metaniobate, lithium sulfate and polyvinylidene fluoride or a combination thereof. A crystal is typically a piezoelectric material, but any material that will contract and expand when an external voltage is applied can be used, if such a material can generate ultrasonic waves described herein and known in the art. Crystals emit ultrasonic waves because the rapid mechanical contraction and expansion of the material moves the medium to generate ultrasonic waves. Conversely, when incoming ultrasonic waves deform the crystal, a current is induced in the material. The material then emits an electrical discharge that can be measured and, ultimately, with B-scan technology, can be used to reconstruct an image. Crystals or combinations of crystals with dipoles that approximate the acoustic impedance of human tissue are preferred, so as to reduce the impedance mismatch at the tissue/probe interface.

Detector refers to any structure capable of measuring an ultrasonic wave or pulse, currently known or developed in the future. Crystals containing dipoles are typically used to measure ultrasonic waves. Crystals, such as piezoelectric crystals, shift in dipole orientation in response to an applied electric current. If the applied electric current fluctuates, the crystals vibrate to cause an ultrasonic wave in a medium. Conversely, crystals vibrate in response to an ultrasonic wave that mechanically deforms the crystals which changes dipole alignment within the crystal. This, in turn, changes the charge distribution to generate an electric current across a crystal's surface. Electrodes connected to electronic circuitry sense a potential difference across the crystal in relation to the incident mechanical pressure. A transducer can be a detector.

Echogenicity refers to the brightness of a tissue in an ultrasonic image relative to the adjacent tissues, typically on a B-scan image. Echogenicity is dependent on the amount of ultrasonic waves reflected by the tissue. Certain tissues are more echogenic than other tissues. Fatty tissue, for example, is more echogenic than muscle tissue. For identical imaging parameters, fatty tissue will thus appear brighter than muscle tissue. Consequently, image brightness can be used to identify different tissues.

Edema refers to a pathologic accumulation of fluid within or between body tissues. Edema fluid can accumulate in the interstitial space (e.g., in an extracellular location) between tissue cells thereby expanding the interstitial space. Edema fluid can also accumulate within the cells.

Frame time, when used in the context of positioning an ultrasonic source, refers to the time that is required to move an ultrasonic source from a first to a second position (or other additional positions) and back using a mechanical motor or other current and future devices. Frame time typically ranges from 10 ms to 2,000 ms. Linear array refers to a transducer design where the crystals are arranged in a linear fashion along one or more axes. Crystals can be fired in sequential, as well as non-sequential and simultaneous firing patterns or a combination thereof. With sequential firing, each crystal can produce an ultrasonic beam and receive a returning echo for data collection. The number of crystals in one array usually determines the number of lines of sight for each recording. With segmental firing, a group or segment of crystals can be activated simultaneously resulting in a deeper near field and a less divergent far field compared with sequential activation. A segmental linear array produces, however, a smaller number of lines of sight when compared to a sequential linear array with the same number of crystals.

Mechanically connected refers to a connection between two or more mechanical components, such as an ultrasonic source having at least two transmission positions. A mechanical connection between two transmission positions may be accomplished using a mechanical motor to rotate or move an ultrasonic source. Optionally the ultrasonic source can be rotated or moved on a track to vary the transmission angle.

Mechanical motor refers to any device that can move a device, such as the ultrasonic source, from at least a first to a second position and, if desired, to additional positions. A mechanical motor may employ a spring-like mechanism to move the ultrasonic source from said first to said second position. A mechanical motor may also employ a hydraulic, a magnetic, an electromagnetic mechanism or any other current and future mechanism that is capable of moving the ultrasonic source from a first to a second position.

Programmed mechanical motor refers to any motor controlled by a program such as a program in a chip or computer. Such motors include mechanical, electrical or hydraulic devices to move an ultrasonic source from a first to a second position, and if desired to additional positions. The program usually defines the frame time that the mechanical motor moves the ultrasonic source from a first to a second position and back. If more than two positions are used, the program can move the ultrasonic source to many different positions, as desired.

Oscillate refers to moving the ultrasonic source repetitively from a first to a second position or other additional positions and moving it back from the second position or other additional positions. Oscillating from the first to the second position and back may be achieved using a mechanical motor. Typically, transducers will be oscillated to vary the transmission angle.

Osteoporosis refers to a condition characterized by low bone mass and microarchitectural deterioration of bone tissue, with a consequent increase of bone fragility and susceptibility to fracture. Osteoporosis presents most commonly with vertebral fractures due to the decrease in bone mineral density and deterioration of structural properties of the bone. The most severe complication is hip fracture due to its high morbidity and mortality.

Plane refers to the surface of a cross-sectional area of tissue interrogated by an ultrasonic probe. In ultrasonic measurements, the portion of the tissue included in the measurement or image is more accurately referred to as a volume. The x-dimension of this volume reflects the length of the tissue plane, i.e. the length of imaged tissue. The x-dimension typically varies between 1 and 10 cm or more. The y-dimension of this volume reflects tissue depth from the plane, e.g. the distance from the skin surface to a reflection point in the tissue. Interrogation of the y-dimension (or depth of the interrogation) depends, among other things, on the type of transducer, the type of tissue, and the frequency with which the ultrasonic beam is transmitted. With higher frequencies, tissue penetration decreases and the maximum depth from the tissue plane will decrease. The y-dimension typically varies between 1 and 30 cm. The z-dimension corresponds to the width of the plane that is interrogated. It typically varies between 1 and 15–20 mm. It is understood that such dimensions are in reference to ultrasonic signals and interrogation. In addition, x, y, and z dimensions are also used with different meaning in the context of positioning probes, and devices for locating probes in different areas of an anatomical region.

Transmission angle refers to the angle of an ultrasonic beam that intersects the object or tissue plane. The transmission angle is normally measured with respect to the object or tissue plane. The object or tissue plane has a reference angle of zero degrees. For example, as the transmission angle increases toward 90 degrees relative to the tissue plane, the ultrasonic beam approaches an orthogonal position relative to the tissue plane. Preferably, ultrasonic measurements are performed when the ultrasonic beam is orthogonal to the plane of the tissue. It is also preferable, in some embodiment of the invention, to vary the transmission angle in a predetermined and controllable manner in order to interrogate anatomical region as a function of a preselected transmission angle(s). Varying the transmission angle is particularly useful for ultrasonic methods used for BUA and SOS measurements. Transmission angle can be varied by changing the position of a transducer with respect to the object to be interrogated.

First position refers to a position of an ultrasonic source (or transducer) that detects or transmits an ultrasonic signal or pulse, respectively. When ultrasonic waves are reflected from different tissue interfaces, reflective distances can be measured to the first position. Typically, the first position will have a predetermined transmission angle associated with it (e.g. 90, 80, 70 or 60 degrees). Reflective distances, can be measured from the first position, and include, but are not limited to, the distance between the ultrasonic source and 1) a skin/soft tissue, 2) a skin/bone or 3) a soft tissue/bone interface. BUA and SOS can also be measured at the first position and if desired compared with measurements from other positions, particularly positions that vary the transmission angle.

Second position refers to a position of an ultrasonic source (or transducer) that transmits or detects an ultrasonic pulse or signal, respectively and having either a different transmission angle from the first position or a different anatomical location than the first position. It is understood that the second position may have the same anatomical location as the first position while having a different transmission angle compared to the first position. When the ultrasonic waves are reflected at the different tissue interfaces, reflective distances can be measured to the second position. Typically, the first position will have a predetermined transmission angle associated with it (e.g. 90, 80, 70 or 60 degrees). Reflective distances can be measured from the second position, and include. but are not limited to, the distance between the ultrasonic source and 1) a skin/soft tissue, 2) a skin/bone or 3) a soft tissue/bone interface. BUA and SOS can also be measured at the second position and if desired compared with measurements from other positions. In some applications it will be desirable for the first and second positions to generally have the same anatomical location while varying the transmission angle. Additional positions can be readily achieved by relocating the ultrasonic source to either vary the anatomical location of interrogation or the transmission angle.

Transmission frequency refers to the frequency of the ultrasonic wave that is being transmitted from the ultrasonic source. Transmission frequency typically ranges between 0.2 MHz and 25 MHz. Higher frequencies usually provide higher spatial resolution. Tissue penetration decreases with higher frequencies. Lower transmission frequencies are generally characterized by lower spatial resolution with improved tissue penetration.

Ultrasonic pulse refers to any ultrasonic wave transmitted by an ultrasonic source. Typically, the pulse will have a predetermined amplitude, frequency, and wave shape. Ultrasonic pulses may range in frequency between 20 kHz and 20 Mhz or higher. Ultrasonic pulses may consist of sine waves with single frequency or varying frequencies, as well as single amplitudes and varying amplitudes. In addition to sine waves, square waves or any other wave pattern may be employed. Square waves may be obtained by adding single-frequency sine waves to other sine waves. The summation of waves can then result in a square wave pattern.

Ultrasonic signal refers to any ultrasonic wave measured by an ultrasonic detector after it has been reflected from the interface of an object or tissue. Ultrasonic signals may range in frequency between 20 kHz and 20 Mhz or higher.

Ultrasonic source refers to any structure capable of generating an ultrasonic wave or pulse, currently known or developed in the future. Crystals containing dipoles are typically used to generate an ultrasonic wave above 20 khz. Crystal, such as piezoelectric crystals, that vibrate in response to an electric current applied to the crystal can be used as an ultrasonic source. In some ultrasonic generators, multiple ultrasonic sources may be arranged in a linear fashion. This arrangement of ultrasonic sources is also referred to as a linear array. With linear arrays, ultrasonic sources are typically fired sequentially, although simultaneous firing of groups of adjacent ultrasonic sources or other firing patterns of individual or groups of ultrasonic sources with various time delays can be achieved as described herein or developed in the art. The time delay between individual or group firings can be used to vary the depth of the beam in an object.

Ultrasonic wave refers to either an ultrasonic signal or pulse.

2.0 INTRODUCTION

The present invention recognizes for the first time that errors arising from overlying soft tissues in ultrasonic measurements of speed of sound and broadband ultrasonic attenuation of trabecular and cortical bone can be corrected by measuring the thickness of the soft tissues that are interposed in the scan beam. Previously, it was not recognized that ultrasonic measurements of soft tissue thickness can be used to correct measured SOS and BUA values for errors introduced by overlying soft tissues. Nor was it recognized that changes in soft tissue thickness is a potential source of decreased accuracy and reproducibility of SOS and BUA measurements in patients with peripheral edema undergoing diuretic or other types of medical treatment of edema with resultant fluctuations in soft tissue thickness. The present invention includes measuring soft tissue thickness using A-scan or B-scan technology in various anatomical locations used for measuring SOS and BUA. The present invention also includes applying appropriate corrections to SOS and BUA based on ultrasonic measurements of soft tissue thickness.

Without limiting aspects of the invention to a particular mechanism of action, the inventors believe that the poor correlations between quantitative ultrasonic techniques and other methods for assessing bone mineral density are often caused by variations in the position of the interrogated bone with respect to the ultrasonic transducers. Sources of such interrogation artifacts include variations in the thickness of the posterior or inferior heel pads that can, in turn, change the position of the calcaneus relative to the ultrasonic transducers. The angle of the tissue with respect to the ultrasonic transducer can also vary even if the transducer is reproducibly located at an interrogation site, which is another potential source of inaccuracy for BUA and SOS measurements. In all cases, differences in the amount of soft tissue interposed in the ultrasonic beam path can ultimately change the speed of sound and broadband ultrasonic attenuation.

In addition, interrogation artifacts in SOS and BUA measurements are particularly pronounced in patients with abnormally increased soft tissue thickness that is commonly encountered in patients suffering from peripheral edema due to cardiovascular, renal, or hepatic disorders (see commonly owned U.S. patent application Ser. No. 08/xxx filed Aug. 19, 1997, by Lang and Mendlein). Previous work failed to recognize that soft tissue swelling or fluctuations in soft tissue thickness in patients with peripheral edema can affect ultrasonic probe position relative to the underlying bone or other underlying structures to be measured. The inventors were the first to recognize that changes in ultrasonic probe position relative to the underlying bone induced by local or generalized soft tissue swelling or fluctuations in soft tissue thickness can reduce short-term and long-term in vivo precision of SOS and BUA measurements. The inventors were also the first to recognize that soft tissue swelling induced changes in ultrasonic probe position relative to the underlying bone can be particularly significant in patients with edema undergoing diuretic or other types of medical treatment of edema with resultant fluctuations in soft tissue thickness.

It was also not previously recognized that changes in soft tissue thickness or local heterogeneity in soft tissue thickness may affect ultrasonic probe position relative to the tissue/structure to be measured in any medical and on-medical ultrasonic applications. The present invention overcomes these limitations by providing devices and methods to correct for changes in tissue structure. The invention also includes methods and devices based on the identification of anatomic landmarks of the structure to be measured or ultrasonic identification of anatomical landmarks adjacent to the structure to be measured with subsequent positioning of the ultrasonic probes relative to these anatomic landmarks. The present invention includes also positioning of ultrasonic probes using landmarks based on either 1) textural information (e.g. density, SOS. BUA or reflective distance or a combination thereof), or 2) 2 or 3 dimensional contour information 3) a combination thereof of the tissue or structure to be measured and of tissues or structures adjacent to the measurement site. The invention also includes methods and devices that are not necessarily based solely on anatomical landmarks, but in some applications can be combined with anatomical landmark embodiments. Preferably, many of the embodiments described herein are designed for automated use with a minimum of operator intervene and preferably remote or computer control of such devices.

By way of introduction and not limitation of the various embodiments of the invention, the invention includes at least seven general aspects:

1) an ultrasonic method of measuring thickness of soft tissues interposed in the ultrasonic beam path in conjunction with measurements of speed of sound and broadband ultrasonic attenuation;

2) a method of correcting measured speed of sound and broadband ultrasonic attenuation for errors introduced by soft tissues interposed in the beam path between the ultrasonic transducers and the object to be measured, 3) an ultrasonic method that identifies anatomic landmarks of the structure to be measured and subsequently positions the ultrasonic probes over the measurement area using these anatomic landmarks;

4) an ultrasonic method that identifies anatomic landmarks adjacent to the structure to be measured and subsequently positions the ultrasonic probe(s) over the measurement area using these anatomic landmarks, 5) an ultrasonic method that identifies anatomic landmarks using different transmission angles;

6) an ultrasonic method that measures BUA or SOS or both using different transmission angles; and 7) devices and systems to achieve or facilitate the methods 1 through 6.

These aspects of the invention, as well as others described herein, can be achieved using the methods and devices described herein. To gain a full appreciation of the scope of the invention, it will be further recognized that various aspects of the invention can be combined to make desirable embodiments of the invention. For example, the aspects 1 and 2 of the invention can be combined with aspects 3 and/or 4 of the invention thereby improving reproducibility of measurements of SOS and BUA even further.

3.0 Automated System for Positioning Ultrasonic Transducers and Related Methods

Predetermined Axis of Transmission and Automated Positioning System

The present invention includes an ultrasonic system for ultrasonic interrogation of tissue. The system is based, in part, on improving ultrasonic measurements by creating a desired axis of transmission or spatial relationship between two ultrasonic transducers and their transmission paths (or reception paths). In the preferred embodiments, the ultrasonic system is adapted to interrogate dense tissues to measure either broadband ultrasonic attenuation or speed of sound.

Typically, such a system includes a first ultrasonic transducer with an axis of transmission in common with a second ultrasonic transducer. The axis of transmission is usually through a portion of a dense tissue and usually the transducers are not permanently fixed but are capable of being repositioned to a predetermined or desired location. The two transducers can be aligned (e.g. mechanically aligned) to have a common axis of transmission. In such situations, the transducers will be generally directed at each other to receive signals from each other. In some applications, the transducers may not have an axis of transmission in common but are instead arranged to each have a predetermined axis of transmission, wherein each transducer may send signals that can be received by the other transducer without having a common axis of transmission. The axis of transmission for each transducer will have an angle of transmission associated with it. Preferably, the transducers are adapted for A scan or B scan mode. Alternatively, tandem transducers can be used wherein each tandem transducer is comprised of 1) a transducer designed for A scan or B scan, and 2) a transducer designed for either broadband ultrasonic attenuation or speed of sound measurements or both. It is understood that a tandem transducer can be paired so that, for instance, the broadband ultrasonic transducer in the first tandem transducer transmits signals and the broadband ultrasonic transducer in the second tandem transducer receives signals.

In some embodiments the axis of transmission of each transducer is predetermined or selected in advance of, or during, transmission or reception of ultrasonic waves. The axis of each transducer can be adjusted or directed to permit either 1) a partial overlap (typically less than about a twenty percent overlap in the acoustic field), 2) a substantial overlap (typically more than about a twenty percent overlap in the acoustic field), 3) a complete overlap (typically more than about a ninety percent overlap in the acoustic field) or 4) no overlap (typically less than about a five percent overlap in the acoustic field) with an axis of transmission of another transducer.

Partial overlap of each axis of transmission facilitates interrogation of tissue from two separate interrogation sites while permitting 1) interrogation of tissue by a single transducer (where there is no substantial overlap of each axis of transmission) or 2) interrogation of tissue by two or more transducers (where there is a partial overlap of each axis of transmission). Typically, the sites of interrogation are at least about 1 cm apart, often at least about 4 cm apart and sometime 6 cm or more cm apart. Transducers at interrogation sites can also be positioned on different faces or sides of a tissue to be interrogated (e.g. on the medial and lateral portion of an appendage). In many of these embodiments the transducers receive signals from each other. Preferably, tandem transducers are used that are adapted or programmed to receive signals from each other. The invention, however, is not limited to such embodiments and a plurality of predetermined axes of transmission for plurality of transducers can be established, wherein the transducers are either adapted not receive signals from other transducers in the system or the signals received and transmitted by each transducer are separately processed. Similarly, substantial or complete overlaps can be achieved if so desired in some embodiments.

Multiple transducers can also be used to create multiple overlaps between each axis of transmission. Each axis of transmission can overlap the same area in a tissue to permit interrogation of the tissue by multiple transducers from separate interrogation sites. For example multiple transducers can be directed to have overlapping axes of transmission to form a desired interrogation volume or path in the tissue (e.g. an interrogation volume substantially shaped like a column or cone). Multiple transducers creating common interrogation volumes from separate interrogation sites using overlapping axes of transmission can improve resolution of internal structures or surfaces.

Without limiting aspects of the invention to a particular mechanism of action, common interrogation volumes can give rise to enhanced, or more precise, ultrasonic measurements due to any one or combination of the following factors. One, reduction in interference and scatter by comparing ultrasonic properties (e.g. ultrasonic data in the form of A scan or B scan) from each transducer and selecting the data with the least amount of interference to use in a reconstruction, map or ultrasonic analysis of the tissue. Two, reduction in ultrasonic wave attenuation (not necessarily broadband ultrasonic attenuation) by comparing ultrasonic properties (e.g. ultrasonic data in the form of A scan or B scan) from each transducer and selecting the data with the least amount of attenuation to use in a reconstruction, map or ultrasonic analysis of the tissue. Three, signal averaging between each transducer participating in constructing the interrogation volume. Such signal averaging would typically account for the different interrogation sites location of each transducer, the amount of axis of transmission overlap or selection of the most accurate data generated for each transducer or a combination thereof. Four, predetermined noise amplitude cancellation by transmitting ultrasonic waves from a first transducer to cancel ultrasonic waves generated from a second transducer that are creating ultrasonic waves or disturbances that causes the noise. Five, unreceived, anticipated signal analysis, which entails analysing the absence of, or change in, signals that are anticipated or predicted to be received by a detector. The absence or change in signals will be indicative of the presence of structures in the path that remove or alter the transmitted ultrasonic signal.

Interference, scattering and attenuation, as well as other sources of error, may vary between transducers because the transducers are located at separate interrogation sites offering different interrogation paths with varying levels of interference, scattering, attenuation, etc. This is based, in part, on the property of ultrasonic hysteresis meaning either 1) the path of an ultrasonic signal transmitted by a transducer through an object of varying compositions with a heterogenous organization returns to the transducer by a different path and with an altered wave form or 2) the path of an ultrasonic signal transmitted by a first transducer through an object of varying compositions with a heterogenous organization will be received by a second transducer by a different path and with an altered wave form compared to an ultrasonic signal transmitted by the second transducer through the same object and received by the first transducer.

For example, a model interrogation site has layers, from the first side of the object to the second side of the object, of A, B, and C. Wherein layer A, B and C all have different speed of sound constants and different microstructures contributing to interference, attenuation and scatter. A signal moving from A to C and back again will have traveled a different path than a signal moving from C to A and back again. A transducer that transmits and receives signals at an interrogation site on the surface of layer A will receive a different set of signals compared to a transducer that transmits and receives signals at an interrogation site on the surface of layer C. Alternatively, a signal moving from A to C will have traveled a different path than a signal moving from C to A. A transducer that receives signals at an interrogation site on the surface of layer C from a transducer sending signals from layer A will receive a different set of signals compared to a transducer that receives signals at an interrogation site on the surface of layer A from a transducer located on the surface of layer C. Consequently, the received signals will have different properties dependent on the path taken through the object.

The different interrogation paths of each transducer offers the ability to sample the data from each path and select the best or appropriate data using defined selection criteria, thereby reducing the source of error or enhancing interrogation of the tissue. For example, in an interrogation of a tibial region a transducer placed on the anterior surface of the tissue may have a sharp and intense reflective surface 1 cm below the surface of the skin indicating bone. The same interrogation site will have little ability to interrogate the muscle "behind" the bone. A second transducer positioned at a second interrogation site on the posterior region of the same tibial region will offer relatively greater ability to interrogate the muscle "behind" the bone compared to the first interrogation site since the muscle is now interrogated using ultrasonic waves that have not been deflected off or attenuated by bone. Data analysis that selects and combines data from each interrogation, and optionally including signal averaging, can be used to generate a reconstruction, map, or ultrasonic analysis of the tissue. Such positioning methods and devices can be used with BUA or SOS, as well as imaging techniques.

Methods and devices used to generate a common interrogation volume, as well as other methods and devices herein, can aid in producing anatomic maps of the tissue or imaging of the tissue. It can also be used in conjunction with invasive procedures as guide or monitor of the progress of the procedure, such as catheterization, trocar based procedures or other types of surgery.

Some examples of different embodiments of tandem transducers related to an axis of transmission are as follows:

1) a common axis of transmission with each transducer substantially orthogonal to the tissue plane,
2) a common axis of transmission with each transducer not substantially orthogonal to the tissue plane (e.g. a first transducer has a transmission angle 75 degrees and a second transducer has a transmission angle of 105 degrees),
3) a predetermined axis of transmission for a first transducer and a second transducer, wherein there is a partial overlap of each predetermined axis of transmission of the first and second transducer and each transducer is substantially orthogonal to the tissue plane, and
4) a predetermined axis of transmission for a first transducer and a second transducer, wherein there is a partial overlap of each predetermined axis of transmission of the first and second transducer and each transducer is not substantially orthogonal to the tissue plane.

Some examples of different embodiments of plurality of transducers (e.g., 2, 3, 4, 5, 6 or more) related to a desired interrogation volume are as follows:

5) a desired interrogation volume generated from a common axis of transmission with each transducer substantially orthogonal to the tissue plane,
6) a desired interrogation volume generated from a plurality of transducers each having an axis of transmission at a predetermined angle with respect to the other transducers or the tissue plane (e.g. a first transducer has a predetermined angle of 60 degrees with respect to a second transducer and a predetermined angle of 120 degrees with respect to a third transducer), and 7) a desired interrogation volume generated from a predetermined axis of transmission for a first transducer and a second transducer, wherein there is a partial overlap of each predetermined axis of transmission of the first and second transducer and each transducer is substantially orthogonal to the tissue plane.

Generally, the system will include an x, y positioner that engages the first ultrasonic transducer and the second ultrasonic transducer to locate each transducer in the appropriate position on the object to be interrogated. Usually, the x, y positioner positions the first ultrasonic transducer and the second ultrasonic transducer while generally maintaining the axis of transmission. The x, y positioner can be designed to include positioning of each transducer independently or positioning of each transducer while simultaneously maintaining a common axis of transmission. The x, y positioner can position the ultrasonic transducer at a desired location along the x axis and y axis of the system. Typically, the x axis is the horizontal axis and the y axis is vertical axis.

A computational unit can be included in the system to manage ultrasonic measurements. Typically, the computational unit is designed to manage ultrasonic signal transmission and reception of the first ultrasonic transducer and the second ultrasonic transducer. It may also be designed to optionally control movement of the x, y positioner. By monitoring signal transmission and reception the computational unit can instruct the x, y positioner to appropriately locate the transducers in order to achieve the desired relationship between the axis of transmission of each transducer. For example, FIG. 1 shows one method of instructing a positioner and interrogating a tissue based on anatomical maps. In many instances the computational unit can be programmed to instruct the x, y positioner to establish a common axis of transmission between the two transducers. As described herein, this is a particularly useful embodiment for broadband ultrasonic attenuation and speed of sound measurements in the human heel. It is also contemplated to use such a system in other anatomical regions where ultrasonic measurements would benefit from controlled or predetermined x, y positioning with two or more probes (e.g. imaging). Typically, the computational unit is programmed to generate anatomical maps using either A scan or B scan data or both. Maps can also be generated using other ultrasound parameters, e.g. Doppler information or flow information acquired with ultrasonic contrast agents.

In greater detail, FIG. 1 shows one embodiment of the invention relating to methods of interrogating a tissue, generating an anatomical map or iustructing a positioner to position a transducer(s). An anatomical map is generated from data obtained by interrogating the tissue at a first transducer(s) position(s) ($n_1$). This can be done using any ultrasonic measurement, such as A scan or B scan or both. A clinical measurement is then made at the first position $n_1$. Any clinical measurement can be used including, SOS. BUA, x-ray, or tomography, as well as a surgical procedure. The process of interrogation, map generation and clinical measurement can be repeated at each subsequent position ($n_1$, $n_2$, . . . ). Optionally, the anatomical map can be compared to a reference map that is usually stored in the computational unit. When a suitable match occurs with the reference map, interrogation can be initiated. Such matches can be based on predetermined match critieria, including anyone or combination of the following criteria: percentage of contour overlap, homology between ultrasonic features in a given map, and the proximity of a set of coordinates in the anatomical map to a defined set of coordinates in the reference map. If no match occurs, the positioner repositions the transducer(s), another interrogation occurs and another map is generated and compared to the reference map. This process can be repeated until the desired match is obtained or until it is determined that no suitable match is possible. Typically, the positioner moves the transducer in increments until the desired location or interrogation site has been reached and the tissue is interrogated for clinical measurement, such as speed of sound or broadband ultrasonic attenuation measurement. Such methods can be adapted as instructions for components of a monitoring system that form a computer program product.

A system that includes one, two, or more ultrasonic transducers, an x,y positioner and a computational unit for signal management and transducer positioning offers a number of advantages. First, transducer positioning can be automatically established without significant operator intervention, as well as with operator direction to a desired position. Second, accuracy and reproducibility of transducer positioning can be improved by appropriately programming the computational unit. Finally, adjustments to transducer positioning during interrogation can be accomplished with minimized interruption of the interrogation process.

The system may optionally include a z positioner that engages and/or positions at least one or more ultrasonic transducers. Preferably, both transducers can be positioned in the z dimension by the z positioner. The z positioner changes the distance of transmission along the axis of transmission between the first ultrasonic transducer and the second ultrasonic transducer. Typically, it changes the distance between the transducer and the interrogation with minimal compression of the interrogated tissue. A pressure sensor can be included on the surface of the transducer or other location to monitor transducer pressure against the interrogated tissue. The pressure sensor can be part of control unit to regulate the amount of transducer pressure at the interrogation site by adjusting the transducer location in the z dimension with the z positioner. If desired, an electronic feedback loop can be included to adjust the transducer position in the z dimension in response to changes in pressure, which could arise from patient movement, tissue swelling or other factors that contribute to changes in transducer pressure. The z positioner can position the ultrasonic transducer at a desired location along the z axis of the system. Typically, the z axis is the axis perpendicular to the x axis which is the horizontal axis, and the y axis is the vertical axis. The z positioner moves the transducer(s) along the z-axis further or closer to the surface of the anatomical location.

The system may optionally include, or be designed as a dedicated device, to achieve speed of sound or broadband ultrasonic attenuation measurements or both. Typically, in such a system the computational unit can estimate speed of sound or broadband ultrasonic attenuation in an interrogated tissue. Preferably, the computational unit can correct the speed of sound or broadband ultrasonic attenuation measurements for errors generated by soft tissue effects. The Examples offer a number of methods for such correction. To accomplish correction methods the system may optionally include a computational unit that comprises a database of correction factors for soft tissue thicknesses and either speed of sound or broadband ultrasonic attenuation measurements. The database may also be comprised of factors related to empirical measurements of soft tissue and broadband ultrasonic attenuation, including historic patient records for comparison.

The x, y positioner included in the system can be any positioner that can accurately position a transducer and maintain the transducer position during interrogation. The x, y positioner can be those known in the art of positioning devices or those developed in the future or disclosed herein. In selecting an x, y positioner the following features should considered and incorporated into the x, y positioner design depending on the application: 1) ease of movement of the positioner preferably with automated control, 2) integration of the positioner into a computer control system, 3) accuracy of positioning (preferably within about ±5 mm, more preferably about ±1 mm and most preferably about ±0.05 mm), 4) speed of achieving a new position should typically be less than 2 to 4 seconds, and 5) ability of the x, y positioner to either locate one transducer or two transducers. It is understood that the x, y positioner may be configured in many arrangements. For instance, the x, y positioner may designed as one positioning system that moves each transducer concurrently or as two x, y positioners that move each transducer independently yet in a coordinated fashion with respect to each transducer. The x, y positioner can be manually controlled, operator computer controlled, or automatically controlled with minimal or no operator intervention or a combination thereof. Preferably, the system is capable of all three modes of operation. If a manual mode is incorporated into the device, the x, y positioner typically includes a grip to manually direct the first and second transducers over a desired anatomic region. Positioners in the art may used as well, such as those provided by Newport (Irvine, Cali.), including stages for rectilinear motion.

In one embodiment the x, y positioner can comprise a frame to maintain the axis of transmission between the first and second ultrasonic transducers. In this embodiment the x, y positioner maintains a "fixed" axis of transmission. Typically, these types of positioners can be less expensive to operate and robust under a variety of clinical conditions because the axis of transmission is fixed, typically during manufacture or in an adjustment protocol. Thus, the x, y positioner is not required to locate the transducer with respect to one another since this is predetermined. Instead the x, y positioner can be primarily designed to locate the transducer in tandem with a fixed common axis of transmission in relation to the anatomic region of interrogation. Typically, the frame engages an x track and the x track engages a y track, thereby an operator can move the first and second ultrasonic transducers manually in either an x or y dimension or combination thereof with respect to an anatomic region. It is understood, however, that such tracks could also be located on separate frames without a fixed common axis of transmission between the two transducers and that a common axis of transmission could be established. The x,y positioner can be designed to accommodate an appendage. Typically, the appendage is held in a predetermined position in the ultrasonic system relative to the x,y positioner. Preferably, the x,y positioner is automatically controlled by the computational unit. In one arrangement, the computational unit instructs an x servo-motor to drive the first ultrasonic transducer and second transducer in the x dimension and a y servo-motor to drive the first ultrasonic transducer and second transducer in the y dimension.

A key and useful feature of some embodiments of the invention is an ultrasonic system wherein the computational unit comprises a computational program to identify an anatomic landmark, as described further herein. For example, the ultrasonic system can be designed wherein the computational unit is designed to instruct the x, y positioner to position the first ultrasonic transducer and the second ultrasonic transducer to interrogate the anatomic landmark. Usually, the x,y positioner generally maintains the axis of transmission between the first ultrasonic transducer and the second ultrasonic transducer and generally through the anatomic landmark.

The anatomical landmark that is selected is part of an anatomical region. Preferably, the anatomical region is selected from the group consisting of a knee, an ankle, and tibia. The x, y positioner can be adapted to accommodate the anatomical site. Preferably, at least the first ultrasonic transducer and the second ultrasonic transducer are adapted for either speed of sound or broadband ultrasonic attenuation (or both) measurements in tissue comprising bone. In another embodiment the computational unit can identify an anatomic landmark in an interrogated tissue and direct the x, y positioner to position over the anatomic landmark, thereby the first ultrasonic transducer and second ultrasonic transducer have an axis of transmission generally through the anatomic landmark.

Figure 3A:
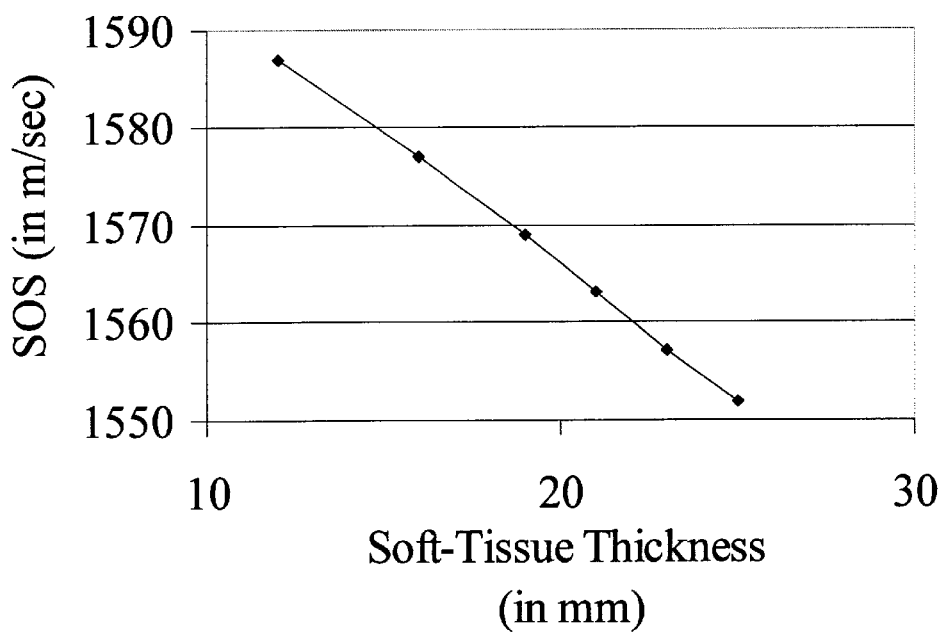
FIG. 3A shows an example demonstrating the influence of soft tissue thickness on ultrasonic measurements of speed of sound. As the thickness of the soft tissue interposed in the scan path increases, measured speed of sound, in this example of the calcaneus, decreases.

As an example of the invention, the use of an x, y positioner either alone or in conjunction with an anatomic landmark can facilitate speed of sound or broadband ultrasonic attenuation measurements in the heel. In FIGS. 3A and B the effect of soft tissue swelling is illustrated in ultrasonic measurements. By including an x, y positioner in an ultrasonic system, the transducers can be positioned to generally maintain an interrogation site that takes into account tissue swelling (or possibly growth). The x, y positioning system can also be used to generate a common axis of transmission for ultrasonic measurements, such as speed of sound measurements or broadband ultrasonic attenuation. By including a landmark detection system, as described herein, even more reproducible and accurate measurements can be made.

Soft tissue Correction

In one embodiment, the invention includes methods and devices for correcting for soft tissue in assessment of bone structure or dense tissue, particularly for osteoporosis. An ultrasonic method for determining broadband ultrasonic attenuation or speed of sound measurements in dense tissues, comprising:

a) interrogating a tissue with an ultrasonic transducer unit adapted for either 1) broadband ultrasonic attenuation or 2) speed of sound measurements or both, b) interrogating the tissue with the ultrasonic transducer to determine soft tissue thickness in the anatomical region with the ultrasonic transducer unit, and c) determining dense tissue broadband ultrasonic attenuation, dense tissue speed of sound or both by correcting for the soft tissue thickness, wherein the determining step generates a dense tissue broadband ultrasonic attenuation value, dense tissue speed of sound value or both that is more indicative of a broadband ultrasonic attenuation value, or speed of sound value in dense tissue than in the absence of correcting for soft tissue thickness.

The ultrasonic method can include a further refined determining step that further comprises adjusting either 1) broadband ultrasonic attenuation or 2) speed of sound in the tissue or both for the soft thickness based on a database of ultrasonic measurements from comparable tissues. The database measurements include soft tissue thickness and either a) broadband ultrasonic attenuation, b) speed of sound or c) both. The determining step can comprise adjusting either 1) broadband ultrasonic attenuation, 2) speed of sound in the tissue or 3) both for the soft thickness based on a correction factor. These methods can be applied at the heel. Often such measurements can include calculating speed of sound for calcaneus tissue using Equation 16 or other equations or methods described herein.

In a related embodiment of the invention, soft tissue thickness measured in a patient is compared to reference soft tissue thickness obtained from a control population (e.g. age-, sex-, race-, or weight-matched normal subjects). Reference soft tissue thickness can be generated by measuring soft tissue thickness in healthy subjects with normal vascular, cardiac, hepatic, or renal function and no other underlying medical condition. Reference soft tissue thicknesses can be expressed as but are not limited to, mean and standard deviation or standard error. Reference soft tissue thicknesses can be obtained independently for patients 15–20, 20–30, 30–40, 40–50, 50–60, 60–70, 70–80, and 80 and more years of age. Reference soft tissue thicknesses for these age groups can be obtained separately for men and women and for race (e.g. Asian, African, Caucasian, and Hispanic subjects). Additionally, reference soft tissue thicknesses can be obtained for different subject weights within each age, sex, and racial subgroup.

Individual patients can be compared to reference soft tissue thickness. If patient's soft tissue thickness is elevated, a correction factor can be applied. The amount/magnitude of correction factor is influenced by the magnitude of increase in soft tissue thickness that can be influenced by the magnitude of fat, fibrous, and muscle tissue contribution. Clinical study groups can be evaluated to generate databases for further study or to generate more refined correction factors. Such study groups include: non-edematous non-osteoporotic premenopausal, non-edematous non-osteoporotic postmenopausal, non-edematous osteoporotic postmenopausal; edematous non-osteoporotic premenopausal, edematous non-osteoporotic postmenopausal, and edematous osteoporotic postmenopausal patients. In each study group the following procedures can be performed for comparison: dual x-ray absorptiometry ("DXA") of the spine, hip, or calcaneus, along with SOS and BUA measurements or quantitative computed tomography ("QCT"). Evening measurements are preferred (the time of maximum edema; and clinically frequent times for outpatient ambulatory office visits).

Without limiting the invention to a particular mechanism of action, the inventors believe that correlation between DXA measurements and SOS and BUA will be better in non-edematous patients than in edematous patients (artificial change of SOS and BUA due to pathologic soft tissue thickening). Correction for soft tissue thickness can also improve the accuracy and discriminatory power of SOS and BUA in non-edematous and edematous patients. Even non-edematous patients will have variations in soft tissue thickness due to diet, obesity, sport related conditioning, hormonal influences, and the like. Such methods can also be used to identify population with an increased or decreased risk of bone fracture, particularly the fracture of the hip, spine, or long bones.

Soft Tissue Correction Devices

Current ultrasonic probes for measuring SOS and BUA are hand positioned using visible or palpable regions on the skin surface (e.g. sole of the fool, posterior margin of the heel). In the calcaneus, pathologic soft tissue thickening, e.g. from tissue edema, will change the position of the calcaneus relative to the transducer on the skin surface. Thus, the transducer(s) will measure over the same external area, but will not measure the same area in the calcaneus. This effect can be particularly pronounced if edema/soft tissue thickness changes between follow-up examinations (e.g. baseline exam in am with little or no edema, follow-up exam in pm with more pronounced edema). Thus, changes in probe position relative to the calcaneus or other bone will affect reproducibility of SOS and BUA as well as other US measurements significantly.

Figure 5A:
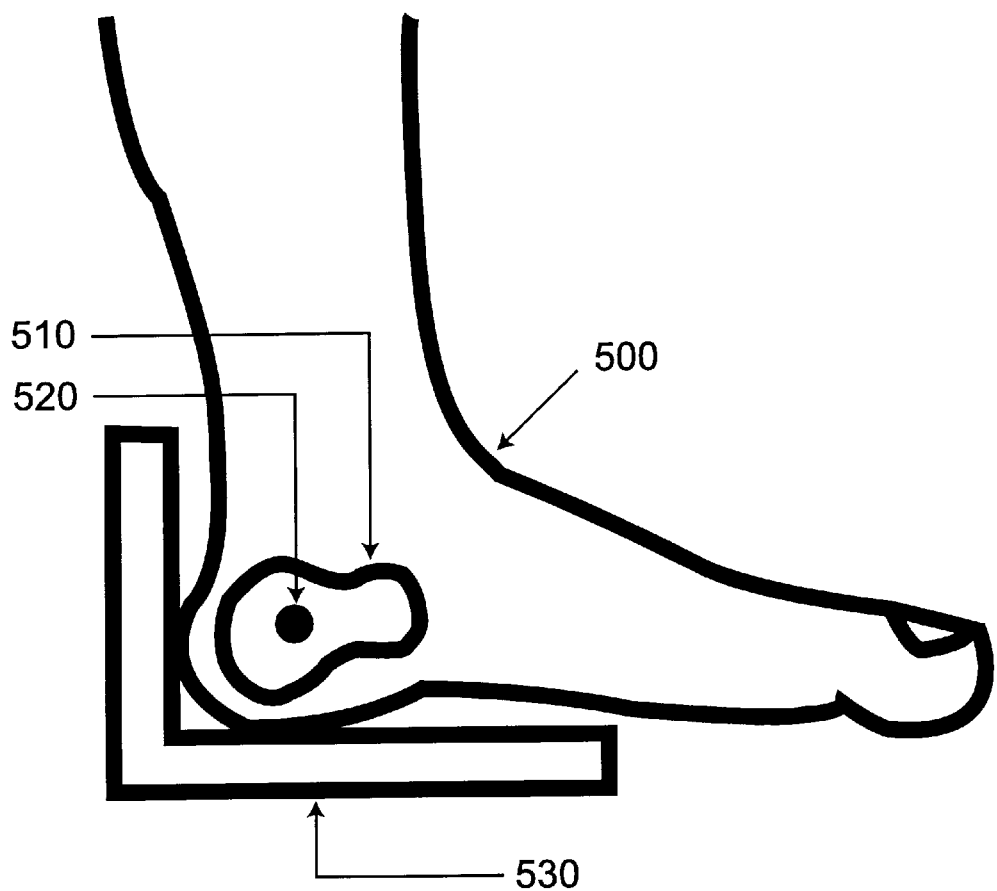
FIG. 5A shows an example of a typical prior art device for measuring the speed of sound or broadband ultrasonic attenuation in a healthy non-edematous patient. The position of the patient's foot 500, of the calcaneus 510, and of the ultrasonic interrogation site 520 are fixed with respect to the device frame 530.

FIG. 5A shows an example of a typical prior art device for measuring the speed of sound or broadband ultrasonic attenuation in a healthy non-edematous patient. The position of the patient's foot 500, of the calcaneus 510, and of the ultrasonic interrogation site 520 are fixed with respect to the device frame 530.

Figure 5B:
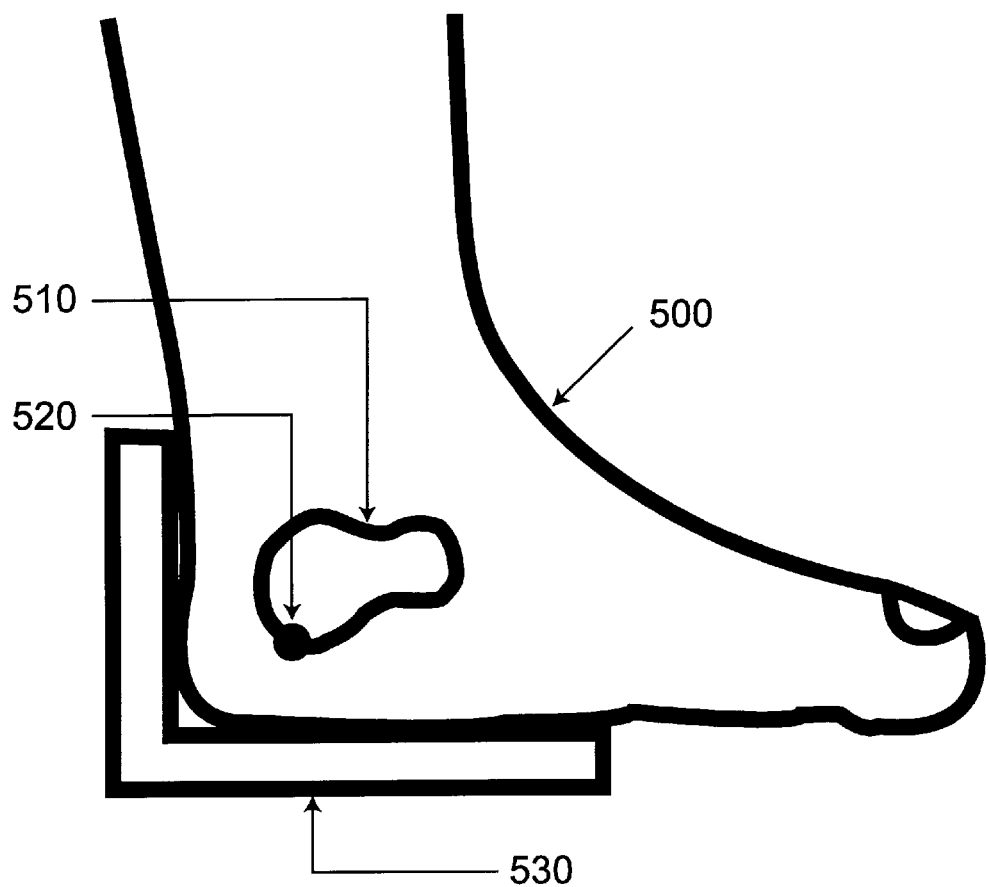
FIG. 5B shows an example of a typical prior art device for measuring the speed of sound or broadband ultrasonic attenuation in a patient with peripheral edema. Edema increases the thickness of the soft tissue inferior and posterior to the calcaneus. Since the position of the ultrasonic interrogation site 520 is fixed relative to the device frame 530, a more inferior and posterior region is measured within the calcaneus 510 when compared to FIG. 5A that is even partially outside the calcaneus 510.

FIG. 5B shows an example of a typical prior art device for measuring the speed of sound or broadband ultrasonic attenuation in a patient with peripheral edema. Edema increases the thickness of the soft tissue inferior and posterior to the calcaneus. Since the position of the ultrasonic interrogation site 520 is fixed relative to the device frame 530, a more inferior and posterior region is measured within the calcaneus 510 when compared to FIG. 5A that is even partially outside the calcaneus 510.

Figure 5C:
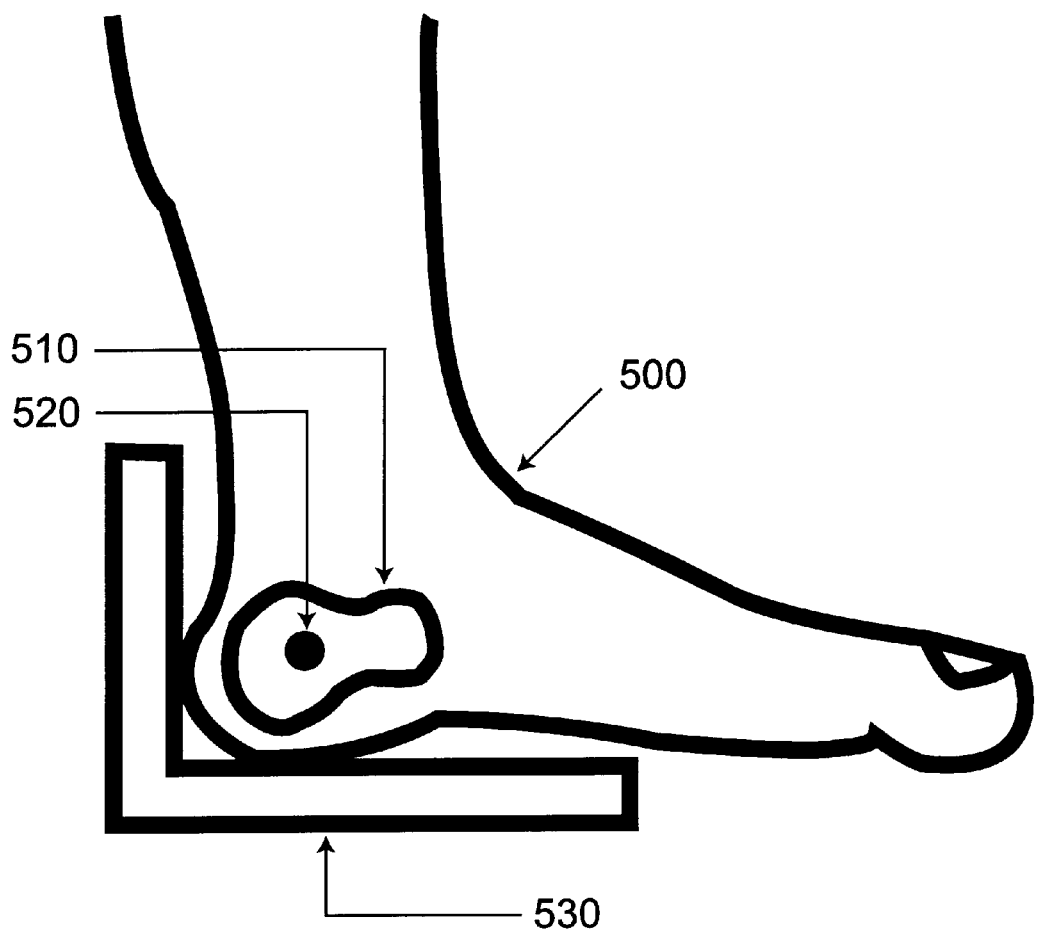
FIG. 5C shows one embodiment of the invention with a probe for measuring for example speed of sound or broadband ultrasonic attenuation of the calcaneus, in this case in a healthy non-edematous patient. The position of the ultrasonic interrogation site 520 is not fixed with respect to the device frame 530 but is determined, for example, based on landmarks or anatomical maps using A-scan or B-scan ultrasonics.

FIG. 5C shows one embodiment of the invention with a probe for measuring for example speed of sound or broadband ultrasonic attenuation of the calcaneus, in this case in a healthy non-edematous patient. The position of the ultrasonic interrogation site 520 is not fixed with respect to the device frame 530 but is determined, for example, based on landmarks or anatomical maps using A-scan or B-scan ultrasonics.

Figure 5D:
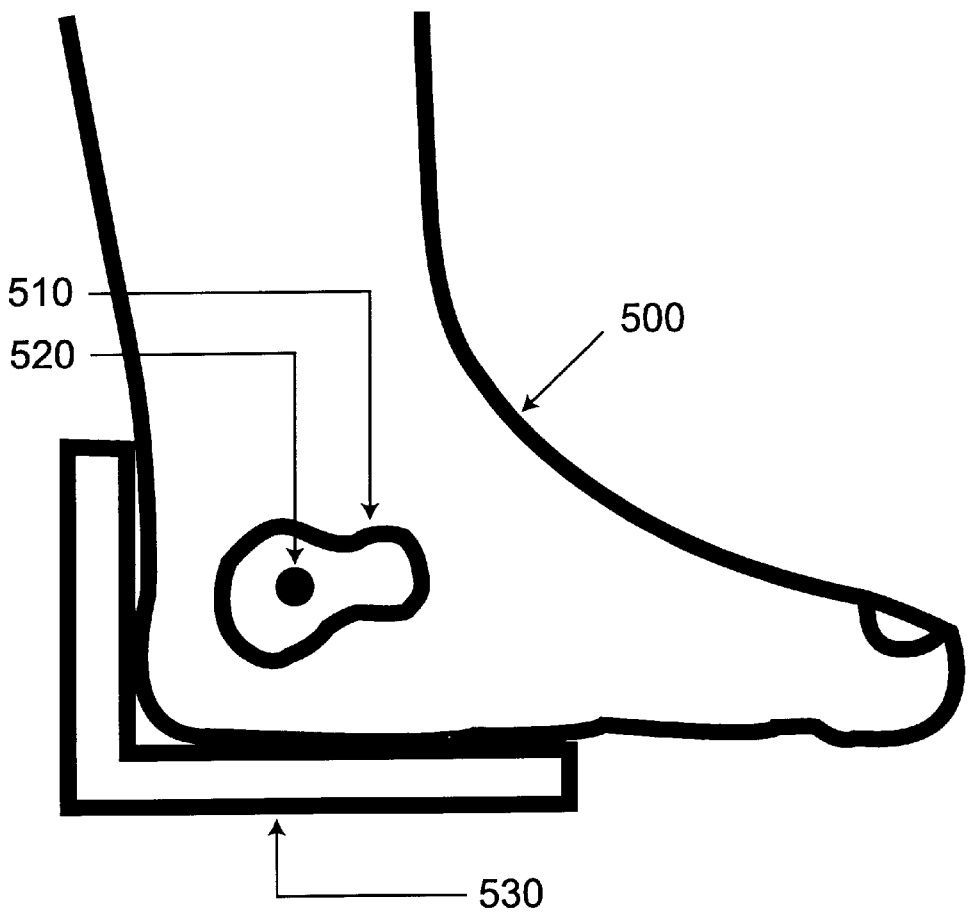
FIG. 5D shows the same embodiment of the invention as seen in FIG. 5C with a probe for measuring for example speed of sound or broadband ultrasonic attenuation of the calcaneus, in this case in a patient with peripheral edema. Edema increases the thickness of the soft tissue inferior and posterior to the calcaneus. Since the position of the ultrasonic interrogation site 520 is not fixed relative to the device frame 530, but is determined, for example, based on landmarks or anatomical maps using A-scan or B-scan ultrasonic, the interrogation site in the calcaneus remains substantially constant in the presence of peripheral edema and does not change significantly compared to conditions illustrated in FIG. 5C.

FIG. 5D shows the same embodiment of the invention as seen in FIG. 5C with a probe for measuring for example speed of sound or broadband ultrasonic attenuation of the calcaneus, in this case in a patient with peripheral edema. Edema increases the thickness of the soft tissue inferior and posterior to the calcaneus. Since the position of the ultrasonic interrogation site 520 is not fixed relative to the device frame 530, but is determined, for example, based on landmarks or anatomical maps using A-scan or B-scan ultrasonics, the interrogation site in the calcaneus remains substantially constant in the presence of peripheral edema and does not change significantly compared to conditions illustrated in FIG. 5C.

Figure 6A:
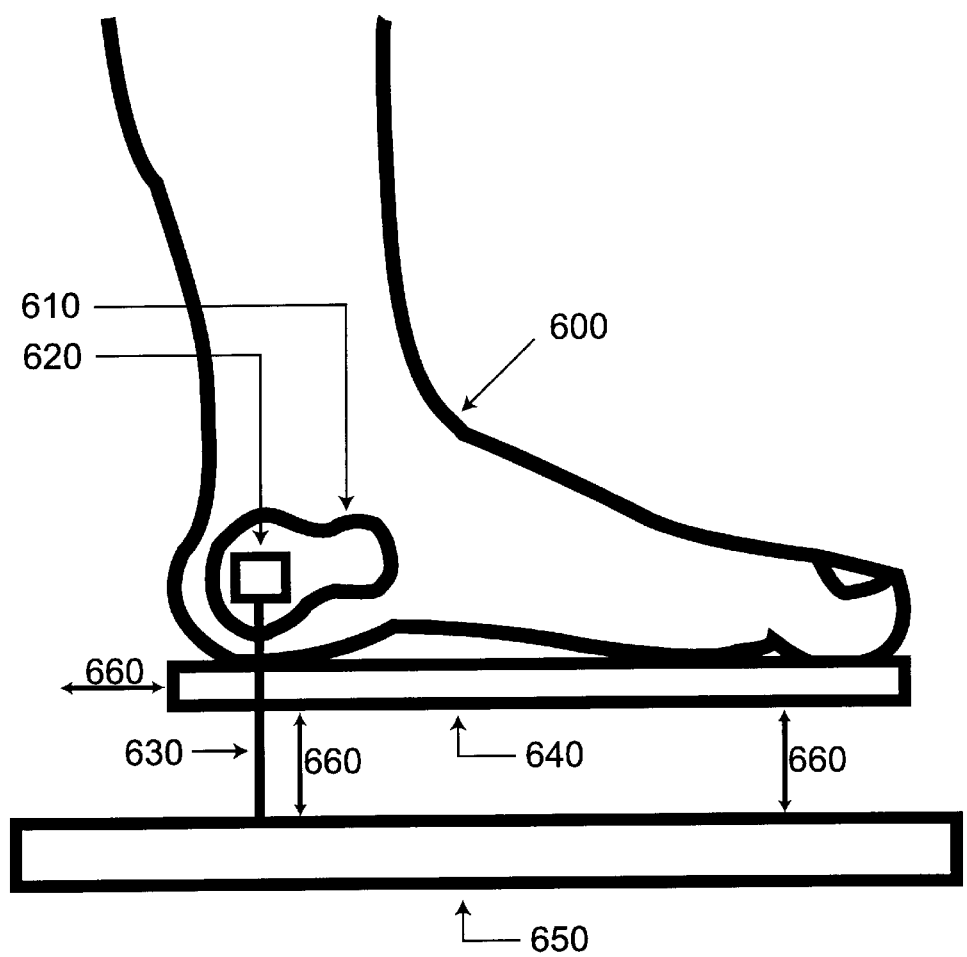
FIG. 6A shows another embodiment of the invention with a device for measuring for example speed of sound or broadband ultrasonic attenuation of the calcaneus, in this case in a healthy non-edematous patient. The position of the patient's foot 600 and of the calcaneus 610 are not fixed with respect to the device frame 650. The ultrasonic transducer 620 is, however, attached 630 to the device frame 650. The foot 600 is placed on a foot holder 640 that can be moved in the x- or y-direction 660. The foot 600 and the calcaneus 610 are positioned relative to the ultrasonic transducer 620 for example based on landmarks or anatomic maps using A-scan or B-scan ultrasonics.

FIG. 6A shows another embodiment of the invention with a device for measuring for example speed of sound or broadband ultrasonic attenuation of the calcaneus, in this case in a healthy non-edematous patient. The position of the patient's foot 600 and of the calcaneus 610 are not fixed with respect to the device frame 650. The ultrasonic transducer 620 is, however, attached 630 to the device frame 650. The foot 600 is placed on a foot holder 640 that can be moved in the x- or y-direction 660. The foot 600 and the calcaneus 610 are positioned relative to the ultrasonic transducer 620 for example based on landmarks or anatomic maps using A-scan or B-scan ultrasonics.

Figure 6B:
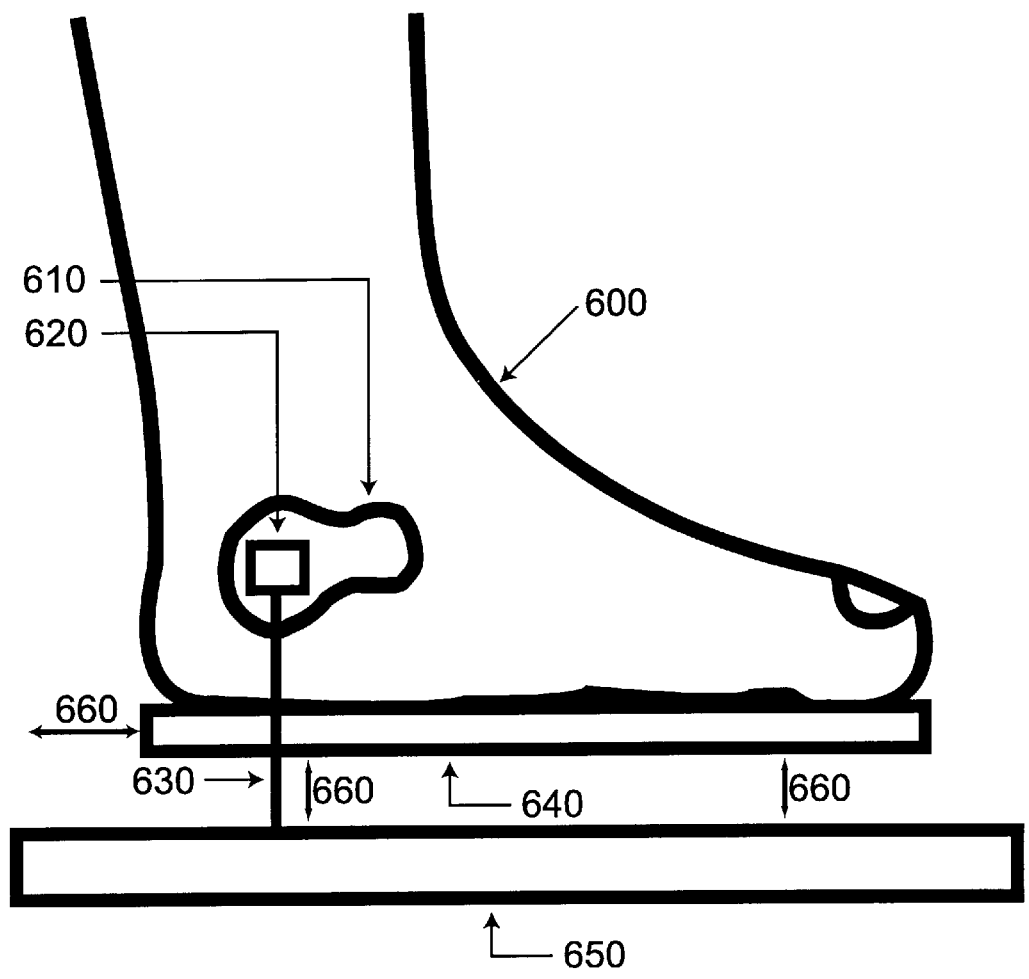
FIG. 6B shows the same embodiment of the invention as demonstrated in FIG. 6A with a probe for measuring for example speed of sound or broadband ultrasonic attenuation of the calcaneus, in this case in a patient with peripheral edema. Since the position of the foot 600 and of the calcaneus 610 is not fixed relative to the device frame 650, but is determined, for example, based on landmarks or anatomical maps using A-scan or B-scan ultrasonics, the interrogation site of the ultrasonic transducer 620 at the calcaneus remains substantially constant in the presence of peripheral edema and does not change significantly when compared to the condition illustrated in FIG. 6A.

FIG. 6B shows the same embodiment of the invention as demonstrated in FIG. 6A with a probe for measuring for example speed of sound or broadband ultrasonic attenuation of the calcaneus, in this case in a patient with peripheral edema. Since the position of the foot 600 and of the calcaneus 610 is not fixed relative to the device frame 650, but is determined, for example, based on landmarks or anatomical maps using A-scan or B-scan ultrasonics, the interrogation site of the ultrasonic transducer 620 at the calcaneus remains substantially constant in the presence of peripheral edema and does not change significantly when compared to the condition illustrated in FIG. 6A.

Figure 7A:
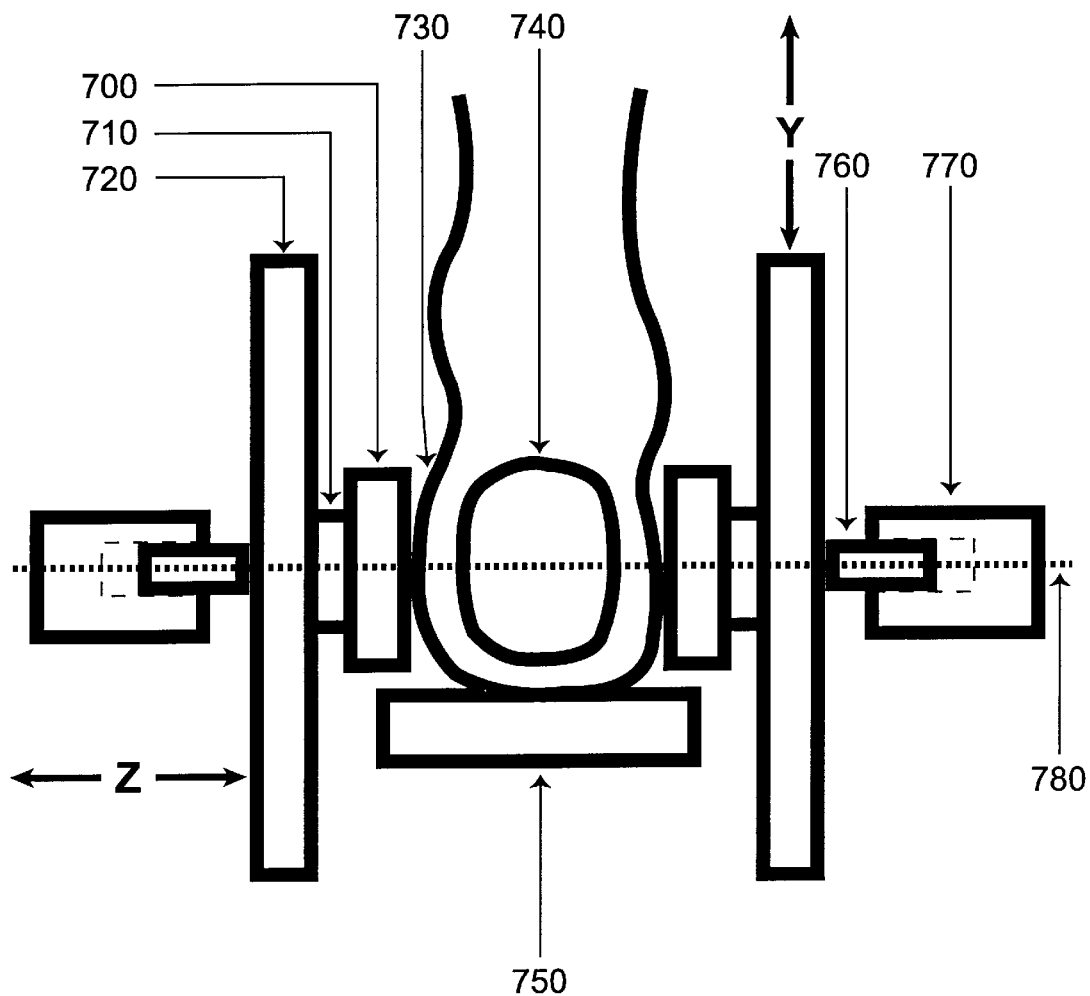
FIG. 7A shows another embodiment of the invention comprising two ultrasonic transducers 700 attached to an x-positioner 710 and a y-positioner 720. The heel 730 and the calcaneus 740 are seated on a foot holder 750. The ultrasonic transducer 700 is brought in contact with the heel 730 using a z-positioner member 760 that can move in and out of a frame 770 continuously or in a stepwise fashion. The ultrasonic transmission axis 780 is also shown.

FIG. 7A shows another embodiment of the invention comprising two ultrasonic transducers 700 attached to an x-positioner 710 and a y-positioner 720. The heel 730 and the calcaneus 740 are seated on a foot holder 750. The ultrasonic transducer 700 is brought in contact with the heel 730 using a z-positioner member 760 that can move in and out of a frame 770 continuously or in a stepwise fashion. The ultrasonic transmission axis 780 is also shown.

Figure 7B:
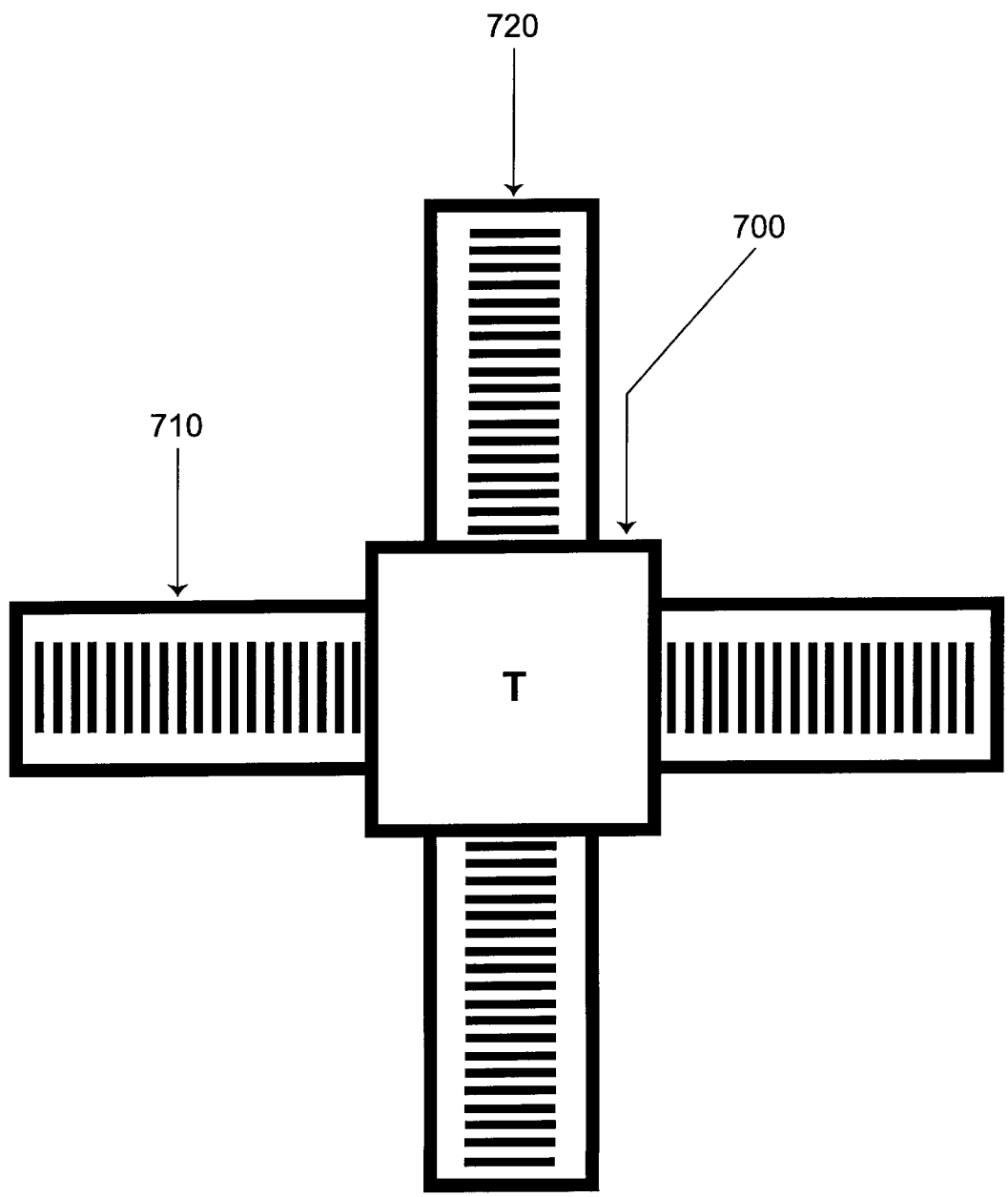
FIG. 7B is a side view of the ultrasonic transducer (T) 700, the x-positioner 710, and the y-positioner 720 shown in FIG. 7A showing the tracks of each postioner. Typically, one positioner will engage the other positioner to permit x, y movement either concurrently (moving in both directions simultaneously) or sequentially (moving in one dimension first and then in a second dimension).

FIG. 7B is a side view of the ultrasonic transducer 700, the x-positioner 710, and the y-positioner 720 shown in FIG. 7A showing the tracks of each postioner. Typically, one positioner will engage the other positioner to permit x, y movement either concurrently (moving in both directions simultaneously) or sequentially (moving in one dimension first and then in a second dimension).

Figure 7C:
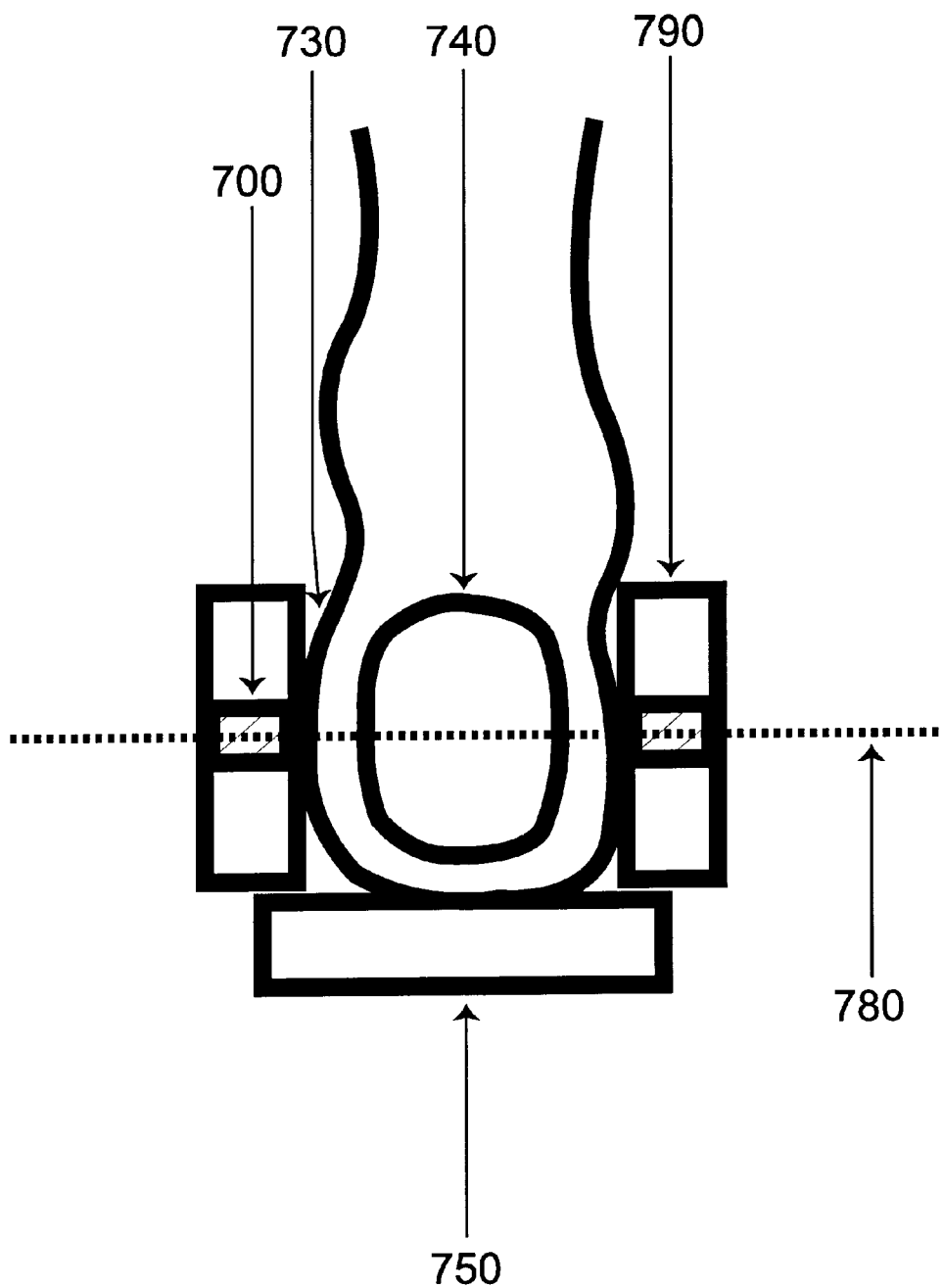
FIG. 7C shows another embodiment of the invention. The ultrasonic transducers 700 are attached to a positioning system 790 that affords movement of the transducers in x, y-, and z-direction, as well as angulation of the transducers 700 and the resultant ultrasonic transmission axis 780. The angulation position of the transducers 700 and the ultrasonic transmission axis 780 is substantially zero.

FIG. 7C shows another embodiment of the invention. The ultrasonic transducers 700 are attached to a positioning system 790 that affords movement of the transducers in x, y, and z-direction, as well as angulation of the transducers 700 and the resultant ultrasonic transmission axis 780. The angulation position of the transducers 700 and the ultrasonic transmission axis 780 is substantially zero.

Figure 7D:
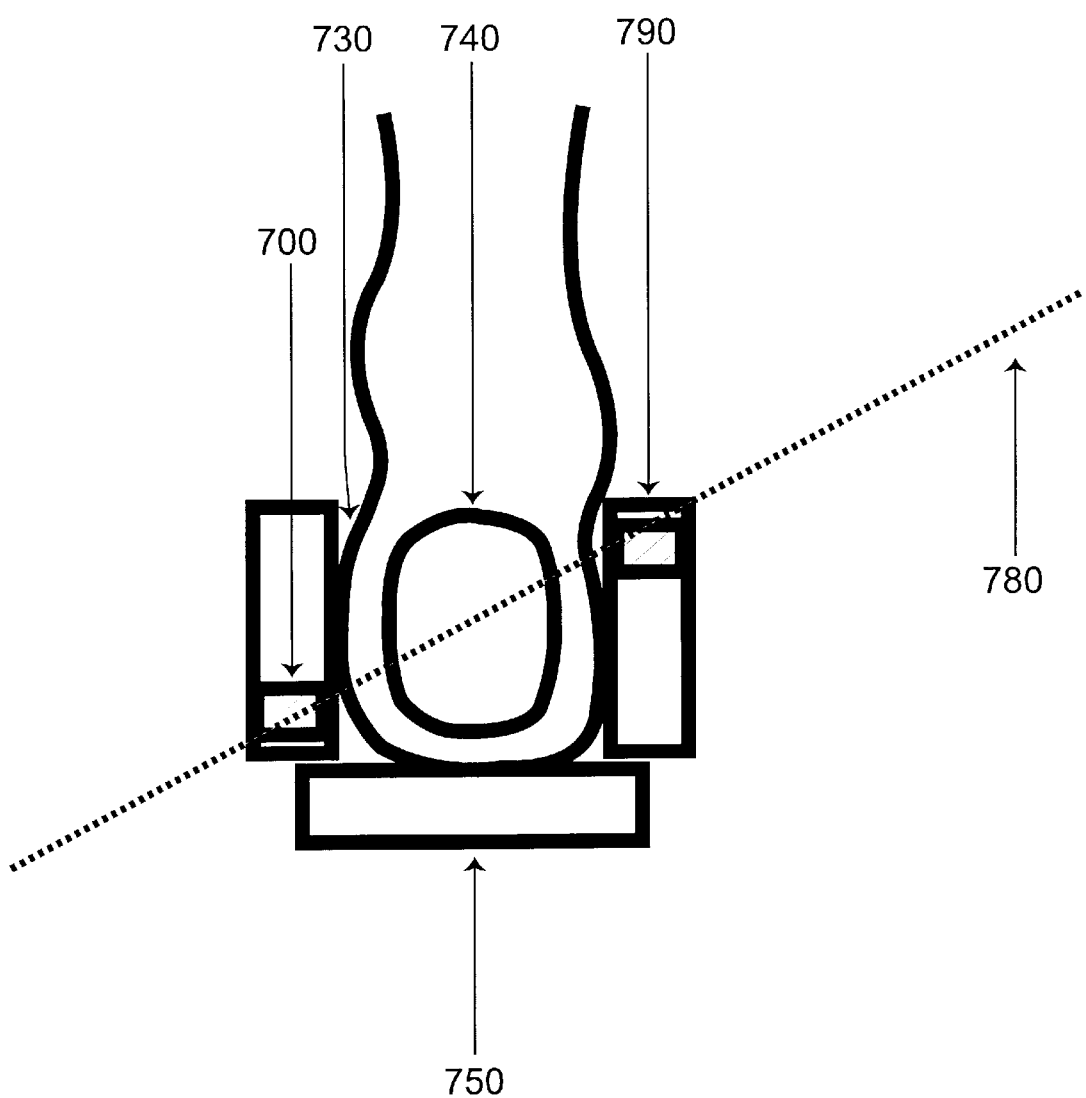
FIG. 7D shows the ultrasonic transducers 700 attached to a positioning system 790 that affords movement of the transducers in x, y-, and z-direction, as well as angulation of the transducers 700 and the resultant ultrasonic transmission axis 780. The angulation position of the transducers 700 and the ultrasonic transmission axis 780 is substantially different from zero.

FIG. 7D shows the ultrasonic transducers 700 attached to a positioning system 790 that affords movement of the transducers in x, y, and z-direction, as well as angulation of the transducers 700 and the resultant ultrasonic transmission axis 780. The angulation position of the transducers 700 and the ultrasonic transmission axis 780 is substantially different from zero.

Figure 7E:
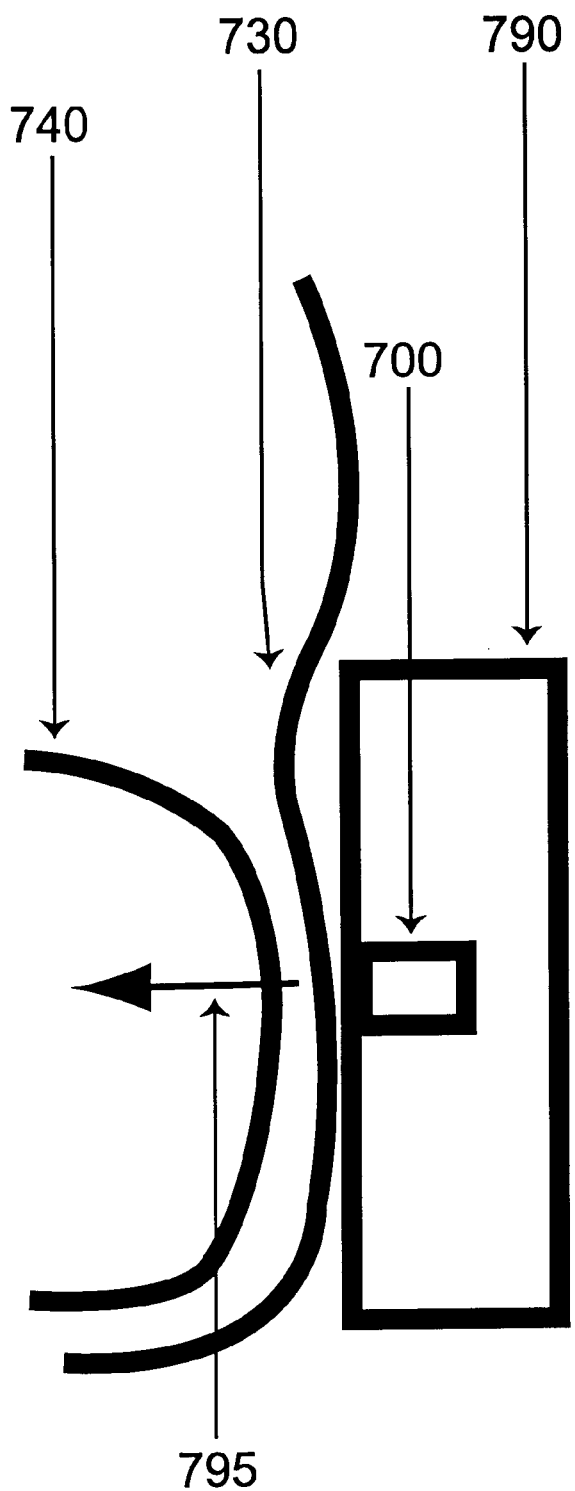
FIG. 7E shows an expanded view of the embodiment presented in FIGS. 7A–D. The ultrasonic transducer 700 is attached to a positioning system 790 that affords movement of the transducers in x, y-, and z-direction, as well as angulation of the transducers 700. The ultrasonic beam 795 has substantially zero angulation.

FIG. 7E shows an expanded view of the embodiment presented in FIGS. 7A–D. The ultrasonic transducer 700 is attached to a positioning system 790 that affords movement of the transducers in x, y, and z-direction, as well as angulation of the transducers 700. The ultrasonic beam 795 has substantially zero angulation.

Figure 7F:
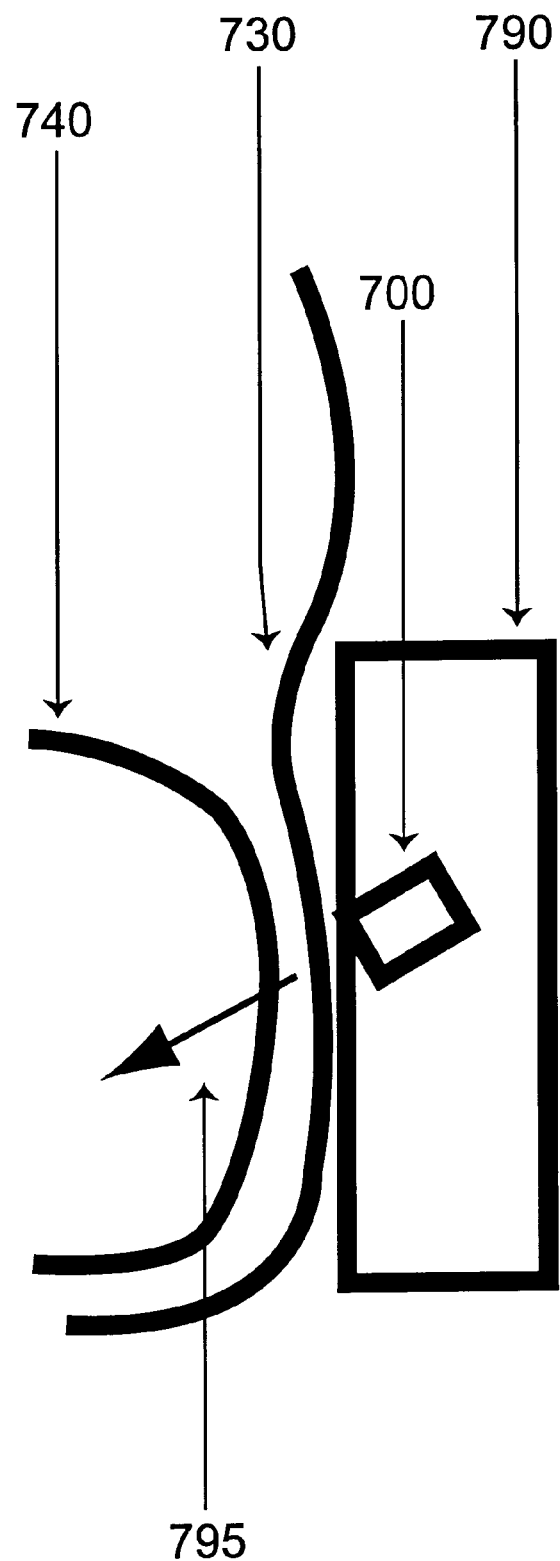
FIG. 7F shows an expanded view of the positioning system 790 and the ultrasonic transducers 700 with inferior angulation of the ultrasonic beam 795.

FIG. 7F shows an expanded view of the positioning system 790 and the ultrasonic transducers 700 with inferior angulation of the ultrasonic beam 795.

Figure 7G:
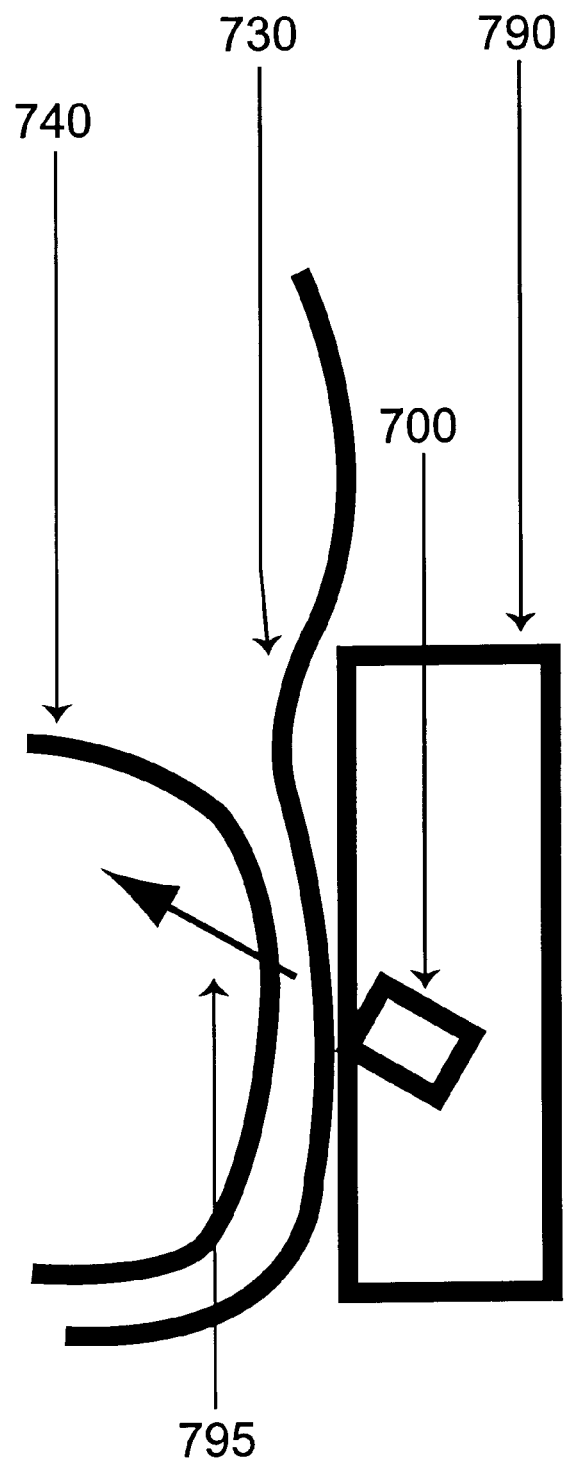
FIG. 7G shows a magnification view of the positioning system 790 and the ultrasonic transducers 700 with superior angulation of the ultrasonic beam 795.

FIG. 7G shows an expanded view of the positioning system 790 and the ultrasonic transducers 700 with superior angulation of the ultrasonic beam 795.

Figure 8A:
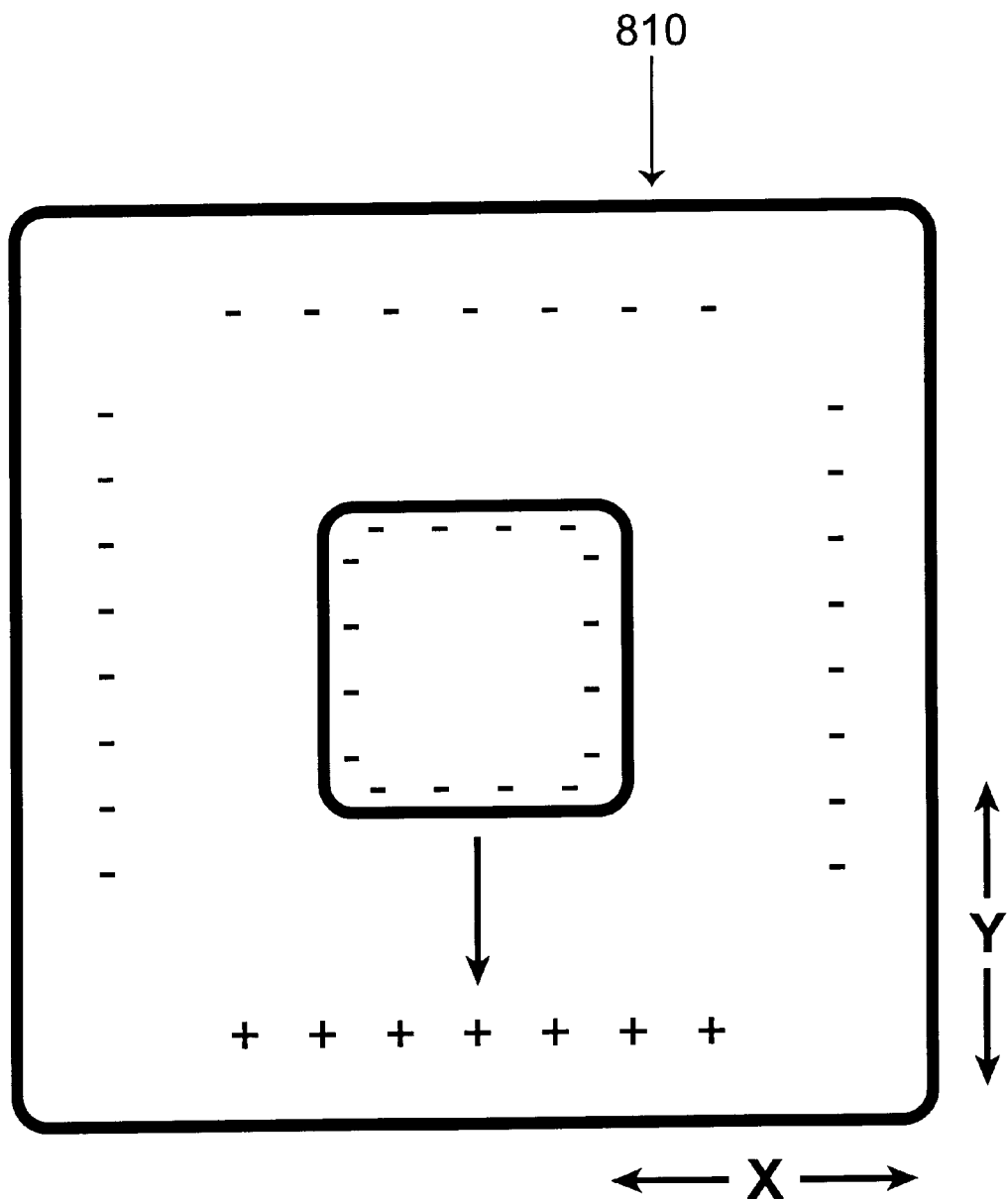
FIG. 8A is a front view of another embodiment of the invention where the transducer 800 is moved along an x, y-positioner 810 using electromagnetic forces rather than using a mechanical or electromechanical x, y-positioner.

FIG. 8A is a front view of another embodiment of the invention where the transducer 800 is moved along an x, y-positioner 810 using electromagnetic forces rather than using a mechanical or electromechanical x, y-positioner.

Figure 8B:
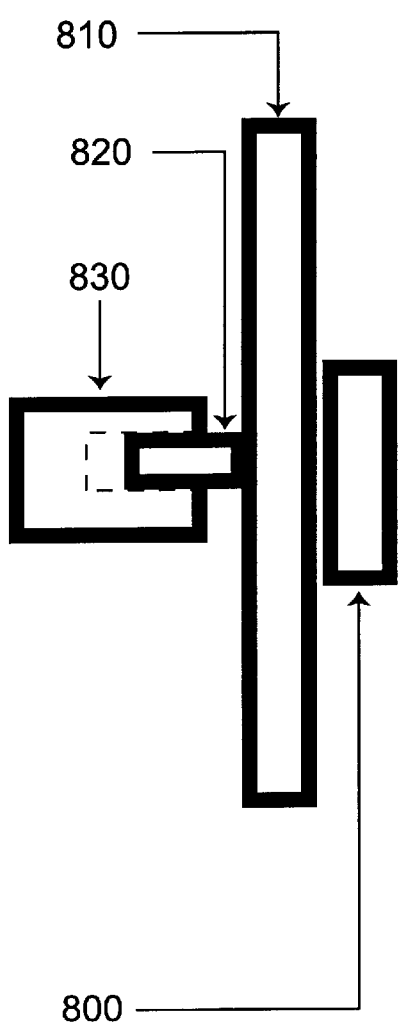
FIG. 8B shows a side view of the transducer 800 and the electromagnetic x, y-positioner 810. The transducer 800 is brought in contact with the heel (not shown) using a z-positioner member 830 that is moved in and out of frame 840.

FIG. 8B shows a side view of the transducer 800 and the electromagnetic x, y-positioner 810. The transducer 800 is brought in contact with the heel (not shown) using a z-positioner member 830 that is moved in and out of frame 840.

Figure 8C:
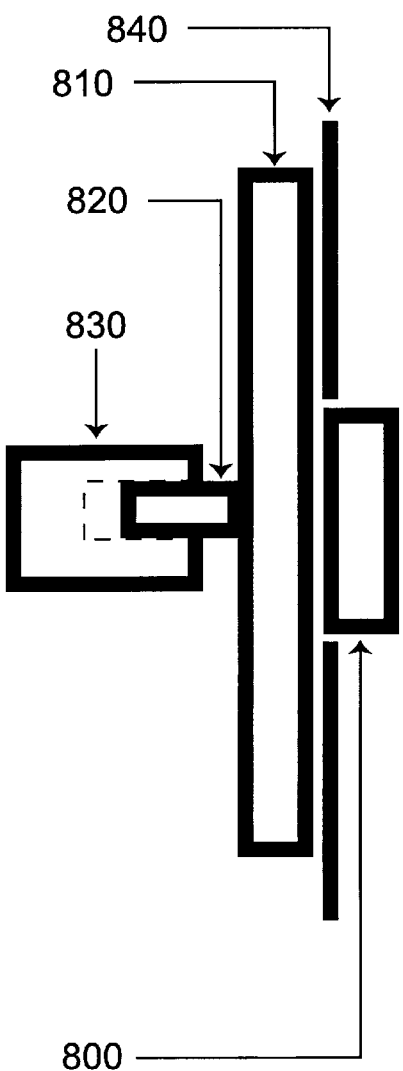
FIG. 8C shows a modification of the embodiment present in FIG. 8B. The sides of the transducer 800 are isolated from the electromagnetic x, y-positioner 810 using a flexible or movable electromagnetic insulator 840.

FIG. 8C shows a modification of the embodiment present in FIG. 8B. The sides of the transducer 800 are isolated from the electromagnetic x, y-positioner 810 using a flexible or movable electromagnetic insulator 840.

Many of the positioning embodiments of the invention can be used to assist in enhancing such measurements and as described further herein anatomical landmarks can also be used to enhance measurements.

For example, in one embodiment an A-scan or B-scan ultrasonic device is used to identify a contour or landmarks of the calcaneus or other bone. Specifically, the posterior and inferior margin or other bony landmarks of the calcaneus (or other bone) are detected and registered spatially, e.g. on a coordinate system in the system computer. The transducer(s) for BUA and SOS measurements are subsequently positioned using the bone margins or landmarks (inferior and posterior or other) as reference points or using the coordinate system. On follow-up examinations in the same patients the system will automatically or using operator assistance find the same bony margins/landmarks and position the transducer(s) over the same measurement site(s) of the calcaneus or other bone that was evaluated during the previous examination (s). This type of positioning ensures reproducible placement of the transducer(s) over the same measurement area of the calcaneus or other bone. In-vivo reproducibility of any type of SOS and BUA will be markedly improved using this technique. This technique is also applicable for improving reproducibility of measurements of soft tissue or internal organs, as described herein.

4.0 ULTRASONIC SYSTEMS AND LANDMARK DETECTION SYSTEMS

The present invention includes an ultrasonic system for ultrasonic interrogation of tissue. The system is based, in part, on improving ultrasonic measurements by creating a anatomical landmark, anatomical maps ("maps") or both. In the preferred embodiments the ultrasonic system is adapted to provide maps and interrogate tissues for either broadband ultrasonic attenuation or speed of sound measurements.

The invention also includes an ultrasonic system for tissue ultrasonic interrogation using anatomic landmarks that can be identified by the system. Such a system can include an ultrasonic transducer unit comprising either 1) a first ultrasonic transducer that can transmit and receive signals or 2) a pair of ultrasonic transducers where a first member of the pair is designed to transmit signals and a second member of the pair is designed to receive signals. A computational unit can be part of the system and is designed to manage ultrasonic signal transmission and reception of the ultrasonic transducer unit and to process signals to identify an anatomical landmark in an anatomical region. For instance, the computational unit is designed to process ultrasonic signals received from the ultrasonic transducer unit to generate an anatomical map of the anatomical region and identify the anatomic landmark within the anatomical region. The map can provide computer stored coordinates to locate the anatomic landmark within the anatomical region for current or future aid in positioning the transducer with x,y positioners, as described herein or known in the art. Preferably, the transducer units and computational unit have adapted A scan or B scan operation and more preferably can be used for measuring other ultrasonic properties as described herein or have transducers adapted to measure such other properties. Preferably, the process of identifying an anatomical landmark is programmed into the computational unit to permit highly automated interrogation. Such an anatomical landmark can either allow an operator to locate a transducer or allow a computer to locate a transducer or some combination thereof.

In addition, echogenic markers can be introduced, either temporarily or permanently, as anatomic landmarks in a predetermined position. Such landmarks include: biocompatible metal probes, needles, stents, or other plastic, metal, or gas containing objects with a securing member to attach to the landmark in the desired position.

Typically, landmarks are based on least one ultrasonic property and preferably two or three or more different properties. For instance, the landmark system may be part of a computational unit further designed to process received ultrasonic signals from the ultrasonic transducer unit to generate at least one data set of an ultrasonic property (e.g. A-scan) and to generate the anatomical map from at least some of the data set. The map itself can be an ultrasonic property correlated with the x, y position of the x, y positioner. It is understood that the data set may have more data than is necessary to generate a particular map or a map may be produced from a selection of data from said data set. In one embodiment the ultrasonic property is selected from the group consisting of broadband ultrasonic attenuation, echogenicity, reflective surfaces, distances from the transducer unit, speed of sound, ultrasonic images, Doppler information and information obtained with ultrasound contrast agents. Combinations of these properties can generate particularly useful maps. For instance, an anatomic landmark may be identified by ultrasonic images in conjunction with echogenic surfaces. Using multiple properties can help tailor the type of landmark desired to be identified. Landmark systems are particularly useful in areas where patient morphology may change but a particular anatomical feature may not, such as dense bone in the heel.

In many embodiments of a landmark system it will be useful to compare landmarks within an anatomical region. The same landmark may be compared at different times (intra-landmark comparison) or one or more landmarks may be compared (inter-landmark comparison). For instance, an intra-landmark comparison can be used during a single interrogation protocol that entails multiple interrogations of the same region with reference to a particular anatomical landmark. The computational unit can also further comprise a database comprising reference anatomical maps and the computational unit is further designed to compare the anatomical map with the reference anatomical map. The reference anatomical map may be historic (from the same or another patient, generated as part of an interrogation protocol), or theoretical or any other type of desired reference map.

Anatomical landmarks are extremely useful in positioning the transducer(s). In an exemplary surgical protocol, landmarks can be identified in the tissue to be examined and during the endoscopic procedure surgical instruments can be manipulated with respect to such landmarks. Computer control of the transducers can maintain visualization of the landmarks during the procedure. In addition, the computational unit can direct instruments or instruct physicians to direct the instruments in relation to the landmarks.

In another embodiment the computational unit directs a positioning unit to position the transducer unit with reference to the anatomical landmark. The transducer can be positioned by an iterative process to find a preprogrammed landmark (e.g. historic) or to identify a landmark by preprogrammed criteria. Typically, the computational unit is designed to instruct the transducer unit to transmit and receive signals after positioning the transducer unit with respect to the anatomical landmark. This process can be repeated and is outlined in FIG. 2.

Figure 2:
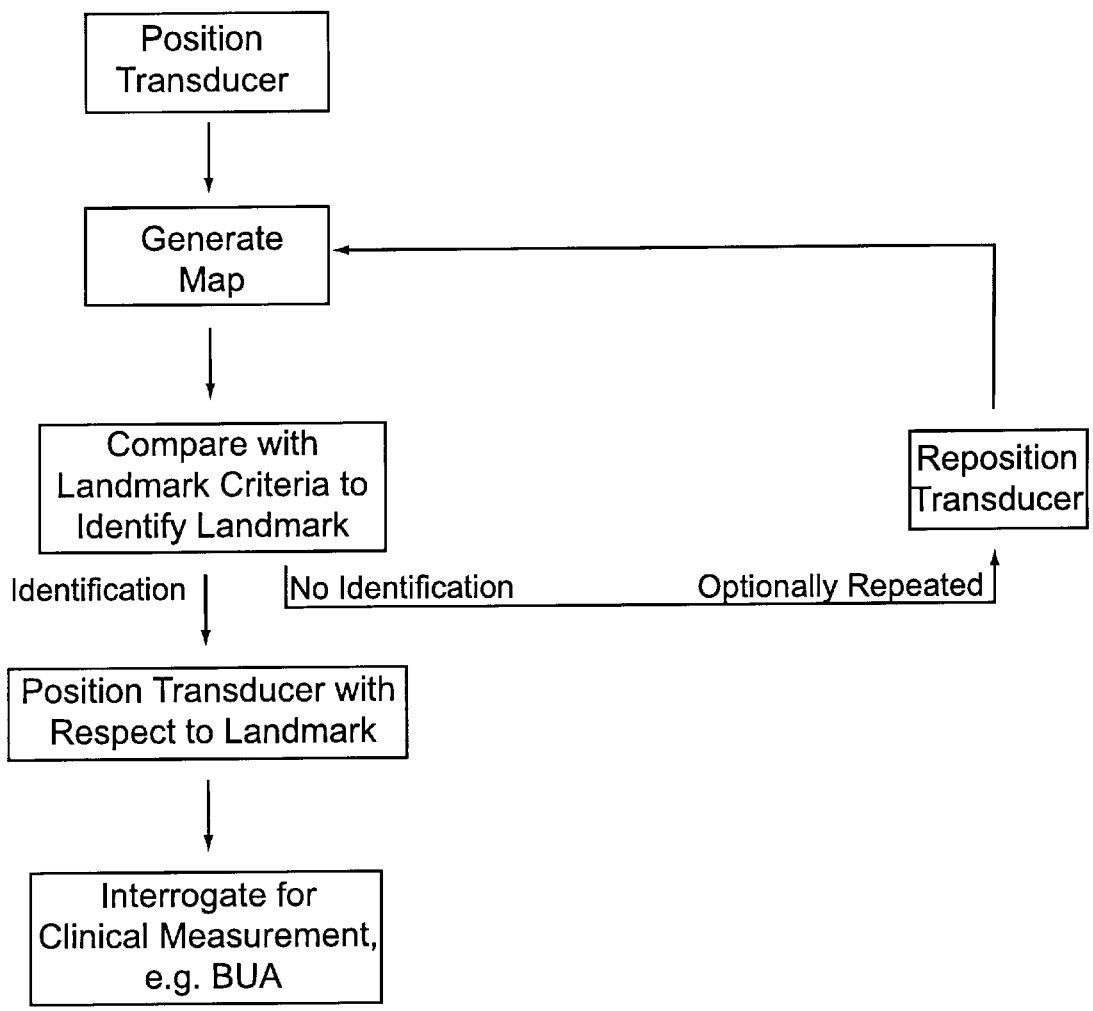
FIG. 2 shows another embodiment of the invention relating to methods of interrogating a tissue, identifying an anatomical landmark or instructing a positioner to position a transducer(s). The transducer(s) is positioned. An anatomical map is generated from data by interrogating the tissue at a first transducer(s) position(s) ($n_1$), for instance using either A scan or B scan or both. A comparison of the map to landmark criteria is then made to identify a landmark at the first position $n_1$. The process of positioning, interrogation, map generation and comparison can be repeated at each subsequent position ($n_1$, $n_2$, . . . ). After a landmark has been identified, a clinical measurement can be intiated.

In greater detail, FIG. 2 shows another embodiment of the invention relating to methods of interrogating a tissue, identifying an anatomical landmark or instructing a positioner to position a transducer(s). The transducer(s) is (are) positioned. An anatomical map is generated from data obtained by interrogating the tissue at a first transducer(s) position(s) ($n_1$). This can be done using any ultrasonic measurement, such as A scan or B scan or both. A comparison of the map to landmark criteria is then made to identify a landmark at the first position $n_1$. The process of positioning, interrogation, map generation and comparison can be repeated at each subsequent position ($n_1$, $n_2$, . . . ). After a landmark has been identified, a clinical measurement or surgical procedure can be initiated. Typically, a computational unit directs a positioning unit to position the transducer unit with reference to an anatomical landmark. The transducer can be positioned by an iterative process to identify a landmark, e.g. based on preprogrammed landmark criteria. Typically, the computational unit is designed to instruct the transducer unit to transmit and receive signals after positioning the transducer unit with respect to the anatomical landmark. Such methods can be adapted as instructions for components of a monitoring system that form a computer program product.

The ultrasonic system can further comprise a positioning unit for changing the spatial relationship between the anatomic landmark in the anatomical region and the ultrasonic transducer unit, thereby permitting interrogation with reference to the anatomic landmark in the anatomical region by positioning the transducer unit with respect to the anatomical landmark. The computational unit can further comprise a display for showing the anatomical map.

Preferably, the positioning unit is selected from the group consisting of a positioning unit that positions the transducer unit, a positioning unit that positions the anatomical region or a positioning unit that can position both. The positioning unit can be operated and designed for manual, computer operator or automatic operation. The positioning unit can be manually operated to interrogate an anatomical region, such as an ankle. Positioning unit can be those devices known in the art or described herein to accomplish such functions.

In one embodiment the invention includes an ultrasonic system for tissue ultrasonic interrogation for broadband ultrasonic attenuation, comprising:

a) a first ultrasonic transducer with a first axis of transmission through a first anatomical region to be interrogated and the first ultrasonic transducer is adapted for longitudinal transmission, b) a second ultrasonic transducer with a second axis of transmission through a second anatomical region to be interrogated and adapted for longitudinal reception, wherein the first anatomical site and the second anatomical site permit monitoring broadband ultrasonic attenuation and speed of sound between the first ultrasonic transducer and the second ultrasonic transducer, c) a positioning unit to position the first ultrasonic transducer with respect to the first anatomical region and to position the second ultrasonic transducer with respect to the second anatomical region, and d) a computational unit designed to manage ultrasonic signal transmission of the first ultrasonic transducer, to manage ultrasonic signal reception of the second ultrasonic transducer and to control the positioning unit.

The transducers are adapted for either longitudinal transmission or reception or both. Longitudinal transmission refers to transmission of signals between two transducers. Longitudinal reception refers to reception of signals between two transducers. Transducers or the computation unit can be adapted for such transmission and reception by including the pulse protocols frequencies and analysis methods. Typically, the positioning system can independently position each transducer to establish a desired spatial relationship between the axis of transmission for each transducer, including a common axis of transmission. For example, the positioning unit can comprise an x, y positioner for the first ultrasonic transducer and the second ultrasonic transducer. Typically, the first axis of transmission is generally the same axis of transmission as the second axis of transmission. Preferably, the ultrasonic system includes a computational unit comprising a computer program product to generate an anatomic landmark to assist in reproducible positioning of the first ultrasonic transducer and the second ultrasonic transducer and the positioning unit comprises a z positioner controlled by the computational unit.

5.0 Methods for Generating or Identifying Anatomical Landmarks

The invention also includes an ultrasonic method for generating an anatomic landmark for ultrasonic interrogation, comprising:

a) positioning, with respect to an anatomical region, an ultrasonic transducer unit comprising either 1) a first ultrasonic transducer that can transmit and receive signals or 2) a pair of ultrasonic transducers where a first member of the pair is designed to transmit signals and a second member of the pair is designed to receive signals, and b) interrogating the anatomical region with the ultrasonic transducer unit, and c) identifying an anatomic landmark in the anatomical region with an ultrasonic property of the anatomical region, and d) optionally storing the anatomic landmark in a storage device.

The ultrasonic method can further comprise the steps of comparing the location and axis of transmission of the ultrasonic transducer unit to the location of the anatomic landmark and positioning the ultrasonic transducer unit to produce an axis of transmission generally through the anatomic landmark. Steps a, b, and c can be optionally repeated. This can increase accuracy or permit close matching of observed landmarks with reference maps or landmarks. Each positioning step can be performed in relation to an anatomic landmark. The positioning steps are typically performed to generate an axis of transmission substantially through the anatomic landmark. Although the transmission axis can be in a predetermined coordinate or desired spatial relationship with respect to the landmark. The positioning steps can be performed to in relation to a reference anatomic landmark of the anatomical region that is stored in retrievable form a storage device.

In some embodiments, it will be desirable to generate anatomical maps and landmarks, as well as images, with signals from multiple transmission and detection angles. Generally it will be desirable to place the probe in a position that is substantially orthogonal to the object plane in order to measure layer thickness accurately. In many situations, it will be desirable to transmit a series of pulses at different transmission angles usually about 5 to 10 degrees apart. This permits generating an image or alternatively a map or landmark from different interrogation paths. Typically, transmission angles can differ in 1, 2, 3, 4, 5, 6, 7, 8, 9 or 10 degree increments or multiples thereof. Preferably, a series of transmission angles will be used, as measured with respect to the object plane, such as 90, 85, 80, 75, 70, 65 and 60 degrees. It will be readily apparent to those skilled in the art that transmission angles of 90, 95, 100, 105, 110, 115 and 120 degrees can also be used. In some embodiments, selection of the transmission angle is based on whether a common axis of transmission is desired.

In various embodiment of the invention, transmission angles can converge or diverge from an ultrasonic source or sources. Generally, there is seldom a limitation as to whether convergent or divergent transmission angles can be used in the invention. Some applications will, however, operate more effectively by selecting the appropriate angle arrangement. To retain a narrower field of interrogation, a single ultrasonic source can be used at relatively small divergent angles, such as no more than about a 20 to 30 degree total divergence in transmission angles. For a wider field of interrogation multiple ultrasonic sources can be used with divergent angles. If a narrow field of interrogation is desired, multiple ultrasonic sources can be used with convergent transmission angles.

To vary transmission angles, typically a first pulse has a first transmission angle with respect to the object plane and a second pulse has a second transmission angle with respect to the object plane, wherein there is a predetermined divergent angle between the first and second pulse or a convergent angle between the first and second pulse. The predetermined divergent or convergent angles can be selected to improve the measurement of a ultrasonic parameters generated in A scan or B scan. The selection of transmission angles typically takes into account the depth in the field where the target reflective layer (or layers) is likely to be located (target reflective layer depth), the likely thickness of the target reflective layer (target reflective layer thickness), object composition and distances between ultrasonic sources (if multiple sources are used). Generally, the total range of transmission angles $\alpha$ will not be greater than 45 degrees, and preferably 30 degrees or less.

The divergent angle separates a first position and second position of an ultrasonic source or sources and the first pulse has a centered first axis of transmission and the second pulse has a centered second axis of transmission, wherein the first and second axis do not converge. Usually the divergent angle between the first and second pulse is between 5 to 90 degrees, and preferably between about 5 and 20 degrees.

The convergent angle separates a first position and second position of an ultrasonic source or sources and the first pulse has a centered first axis of transmission and the second pulse has a centered second axis of transmission, wherein the first and second axis converge. Usually the convergent angle between the first and second pulse is between 5 to 90 degrees, and preferably between about 5 and 20 degrees.

Different transmission angles can be accomplished by any method known, developed in the art or in the future or described herein. Typically, the invention includes three different methods (with the corresponding devices) for varying the transmission angle: 1) mechanically changing position of the transducer(s) with respect to the plane of the tissue, 2) providing multiple transducers with predetermined positions that correspond to predetermined transmission angles and 3) steering ultrasonic beams from multiple ultrasonic sources (typically arrays) with predetermined firing sequences. For cost effective production of devices only one of these methods will typically be used in a device. If more sophisticated devices are desired, such methods can also be combined to gain the benefit of the different methods.

To vary transmission angles using a mechanical device, typically the first and second pulses are from a first ultrasonic generator. The first generator has at least a first and a second position. The first and second position are mechanically connected. The generator is guided from the first position to the second position with a mechanical connection. The first and second position (or more positions for more transmission angles) for the ultrasonic generator can be connected using any connection that changes the transmission angle of the ultrasonic generator in an accurate and controllable fashion. Typically, a sweep through all of the desired positions, either in increments or continuously, should be completed within about 0.02 to 2 seconds, preferably within 200 to 500 milliseconds and more preferably within 20 to 200 milliseconds. These time values also apply to other methods of varying the transmission angle. Such a device can be mounted on or engaged by an x, y positioner to locate the tranducers at a desired anatomical region.

In one embodiment, the invention utilizes a mechanical connection comprising a mechanical motor that can oscillate a generator(s) at least once from the first to the second position (or more positions) in order to vary the transmission angle. This device can be used to create maps, identify anatomical landmarks, and measure BUA or SOS or other ultrasonic methods described herein. The mechanical motor typically provides a frame time of oscillation from 10 to 2500 ms. Any mechanical motor that can produce a position change in such a time frame in response to an electrical command signal and can be adapted for use in a hand-held probe can be preferably used to vary the transmission angle of ultrasonic generators, such as crystals or arrays of crystals. Such a device can be mounted on or engaged by an x, y positioner to locate the tranducers at a desired anatomical region.

In one design the mechanical motor has at least a first and second magnet to move the ultrasonic generator on a track, and the generator further comprises a magnetic source or magnetically attractive material that magnetically communicates with the first or second magnet to change the transmission angle. Magnetic switching of an ultrasonic generator position is particularly desirable because the magnet can be turned off and on relatively rapidly, and directed to change polarity relatively rapidly. Such magnetic systems can provide smooth position changes and relatively noise free performance. The track can be any mechanical device that directs the ultrasonic generator between positions. In some instances the track will comprise a groove that engages the ultrasonic generator and permits the ultrasonic generator to pivot around an axis to allow for the probe to sweep across the desired transmission angles. First and second magnet refers to magnets that can be used to move an ultrasonic source from a first to a second position. Magnets may be permanent or induced by applying an electric current to the appropriate electronic device. For example, an electric current can be applied to a wire arranged in a loop or coil-like configuration and the magnetic field created can be controlled by a predetermined electrical switch. The current induces a magnetic field that can be manipulated depending on the pattern of applied current or by the design of the coil or both. Additional magnets can be used for additional position for multiple placement.

In another embodiment, the invention utilizes permanently fixed ultrasonic generators with different, individual transmission angles to accomplish mapping, anatomical landmarks, BUA or SOS, or other ultrasonic methods described herein. Typically, a first pulse is from a first ultrasonic generator and second pulse is from a second ultrasonic generator, wherein the first and second ultrasonic generators are permanently fixed in a first and a second position. More than two ultrasonic generators can be used as well but usually not more than about 10 ultrasonic generators will be used in this embodiment., unless they are arrays of crystals.

In another embodiment, the invention utilizes predetermined patterns of ultrasonic source activation that result in different transmission angles to accomplish mapping, anatomical landmarks, BUA or SOS, or other ultrasonic methods described herein. For example, a predetermined pattern of ultrasonic source activation can comprise 1) a first series of trigger pulses that sequentially fires an array of ultrasonic crystals starting from a first end to a second end of the array and 2) a series of trigger pulses that sequentially fires the array from a second end to a first end of the array. The first series of pulses have a biased direction along a first portion of the field of the interrogated object, i.e. the beams are steered to one side of the field. This sequence of pulses can be repeated at different time frames in order to change the average transmission beam angle. Similarly, the second series of pulses have a biased direction along a second portion of the field of the interrogated object, i.e. the beams are steered to a second side of the field. This sequence of pulses can be repeated at different time frames in order to change the average beam angle. With linear arrays this method permits the use of either divergent or convergent transmission angles without mechanically moving the ultrasonic source to change the transmission angle. Averaged beams obtained by this method with different transmission angles can then be used to calculate BUA or SOS or other ultrasonic methods as described herein.

As part of the predetermined pattern of ultrasonic source activation, simultaneous triggering pulses may also be used in conjunction with sequential firing patterns. Simultaneous firing of the ultrasonic sources effectively provides a series of beams, which can be optionally averaged, to provide orthogonal probe position relative to a reference plane. When the ultrasonic source is orthogonal to the object/tissue plane, the transmission angle of simultaneously fired beams will be ninety degrees. If the probe has a non-orthogonal position, then the transmission will be more or less than ninety degrees. By comparing the signals generated from sequentially fired pulses to simultaneously fired pulses, the deviation from an orthogonal probe position can be calculated to accomplish mapping, anatomical landmarks, BUA or SOS or other ultrasonic methods described herein. Comparison of ultrasonic parameter (e.g. BUA or SOS) from the averaged signals of both the sequentially generated pulses and the simultaneously generated pulses will be indicative of the difference in tissue structure ascertained at different transmission angles. If so desired, this information can be transmitted back to the operator, for instance on a monitor, to alert the operator to tissue abnormalities or status. Once the operator has evaluated the results, the operator may instruct the system to adjust the probe to achieve orthogonal probe alignment for interrogation of that particular tissue.

The trigger pulses described herein can be particularly optimized to enhance measurement of BUA or SOS in vivo, such as in humans or other objects described herein. To steer a series of beams to create an averaged beam with a specific transmission angle, each ultrasonic crystal is triggered with a 1 $\mu$s to 500 $\mu$s delay between the firing of each crystal. By increasing the delay between firing each crystal, the depth of interrogation and the transmission angle of the averaged beam can be changed. Ultimately, depth of interrogation will be limited by the dimensions of the transducer near and far field (Bushberg, J. T., Seibert, J. A., Leidholdt, E. M., Boone, J. M., The Essential Physics of Medical Imaging 1–742 (1994)). The trigger pulses are timed to delay, such as an exponential delay, the firing of the crystals (crystals 1–5) over a 15 $\mu$sec time period. The firing sequence causes a delay across the array in order to steer to the target and provide an averaged beam (of five beams in this example) with a predetermined transmission angle illustrated as 75 degrees.

EXAMPLES

The following materials and methods are exemplary of the materials and methods that can be used to achieve the results described herein. These examples are for illustrative purposes only, and are not to be construed as limiting the appended claims. One skilled in the art will readily recognize substitute materials and methods.

General Materials and Methods

In vivo ultrasonic measurements are performed using a prototype ultrasonic system capable of measuring speed of sound and broadband ultrasonic attenuation in the heel region. The device is also capable of measuring distances between different acoustic/tissue interfaces using A-scan technique.

The ultrasonic system consists of two ultrasonic sources mounted on a U-shaped plastic frame. A hinge is located in the center portion of the U-shaped plastic frame that allows for adjusting the distance between the ultrasonic transducers for each individual patient. The physical distance separating both transducers is registered for each patient using an electronic system that employs a potentiometer. The U-shaped plastic frame is connected to a plastic housing on which the patient can rest the fore- and mid-foot and in particular the heel comfortably. The ultrasonic sources are placed by the operator on the left and the right side of the foot in the heel region. An ultrasonic gel is used for acoustic coupling. The operator adjusts the frame and the attached ultrasonic sources visually so that they are flush with the skin and near perpendicular to the skin surface.

The ultrasonic system is designed with a central processing unit responsible for pulsing the ultrasonic transducer(s) and crystal(s), registering signals returned from the transducer, preamplification of the electronic signal, time gain compensation, signal compression, signal rectification, demodulation, and envelope detection, signal rejection, signal processing, analysis and display of SOS, BUA, and soft tissue and bone distance measurements. Transducers operate at a center frequency of 1 Mhz. However, transducer center frequency can be switched from 1 to 0.5 MHz. As the interrogation frequency of the micro-transducer decreases, generally, the ability to resolve reflective surfaces at deeper depths improves. The lower frequency is used in obese or edematous patients in whom tissue penetration with the 1 MHz probe is insufficient.

With each measurement the device registers initially the physical distance between both transducers. The device then measures (a) speed of sound, (b) broadband ultrasonic attenuation, and (c) soft tissue thickness on the medial and lateral side of the heel. Broadband ultrasonic attenuation is calculated by subtracting the amplitude spectrum of a patient from one obtained in a reference material (e.g. de-gassed water).

As an alternative to ultrasonic distance measurements using A-scan technique, ultrasonic measurements can also be performed using another prototype system that is capable of two-dimensional image acquisition and display using B-scan technology in addition to SOS and BUA measurements. This ultrasonic system also uses two or more ultrasonic sources mounted on a hinged, U-shaped plastic frame. The physical distance separating both transducers is registered for each patient using an electronic system. After positioning of the patient and the transducers and application of the acoustic coupling gel, data are acquired in B-scan mode. Two-dimensional gray-scale images of the various tissue layers are obtained. Images are displayed on a computer monitor attached to the scanner hardware. Distance measurements are performed by saving a representative image displaying the various tissue layers, e.g. skin, subcutaneous fat and bone, on the display monitor. A trained physician or operator identifies the various tissue interfaces visually and places cursors manually at the probe/skin and the soft tissue/bone or other interfaces. Software provided with the ultrasonic scanner is then used to calculate the distance between the cursors. All measurements are expressed in mm.

All experiments performed on animal subjects (including humans) shall be performed with the highest ethical and medical standards and in accordance with the relevant laws, guidelines and regulations of the relevant governing jurisdiction(s) or professional association(s), including, where appropriate, compliance under 45 CFR 46 relating to United States federal policy for the protection of human subjects.

Example 1

Computational Correction of Tissue Edema Induced Changes in Speed of Sound and Broadband Ultrasonic Attenuation of the Calcaneus This example documents, among other things, that ultrasonic measurements of speed of sound and broadband ultrasonic attenuation are significantly affected by tissue edema. Such edema is frequently encountered in a large variety of medical conditions. Patients with compromised cardiac function, compromised renal function, compromised hepatic function, or compromised vascular function frequently develop tissue edema in the lower extremities. This example also documents that the accuracy of speed of sound and broadband ultrasonic attenuation measurements can be improved by measuring the thickness of the soft tissue that overlies the calcaneus in the beam path and by correcting for the error in SOS and BUA of the calcaneus caused by such soft tissue.

Speed of sound and broadband ultrasonic attenuation measurements are performed in a 35 or 38 year old healthy male volunteer.

Ultrasonic measurements are performed using a prototype ultrasonic system that is capable of two-dimensional image acquisition and display using B-scan technology in addition to SOS and BUA measurements. The volunteer's foot is placed in the ultrasonic system so that it rests inferiorly and posteriorly on the heel pad of the device (see FIG. 5C). The measurement site is marked on the skin with india ink on the left and right side of the heel. A small amount of acoustic coupling gel is applied to the volunteer's skin and the ultrasonic transducers are placed against the skin at the measurement site.

Two-dimensional gray-scale images of the heel are obtained at the measurement site. The distance from the probe/skin interface to the soft tissue/bone interface, i.e. the soft tissue thickness, is measured on the left and the right side of the heel at the measurement site. The sum of the soft tissue thickness measured on the left and the right side of the heel is calculated. SOS and BUA are measured in the same location.

The volunteer's foot is removed from the ultrasonic device. The measurement site at the medial and the lateral aspect of the heel is then cleaned with iodine solution for disinfection. A 20 cc syringe is then filled with 1% Xylocaine solution (Astra Pharmaceuticals, Westborough, Mass. 01581). A sterile 25 Gauge needle is attached to the syringe. The needle is inserted into the subcutaneous tissue of the foot and 1 cc of Xylocaine solution is injected into the tissue at the measurement site on the left side of the heel followed by injection of 1 cc of Xylocaine solution on the right side of the heel.

The volunteer's foot is placed back in the ultrasonic device. Transducers are positioned at the measurement site on the left and right side of the heel as described above and ultrasonic soft tissue distance measurements and measurements of SOS and BUA are repeated.

This experiment is repeated for multiple injection volumes. Injected volumes are increased by 1 cc with each new experiment on each side up to a total injected volume of 5 cc on each side.

Figure 4A:
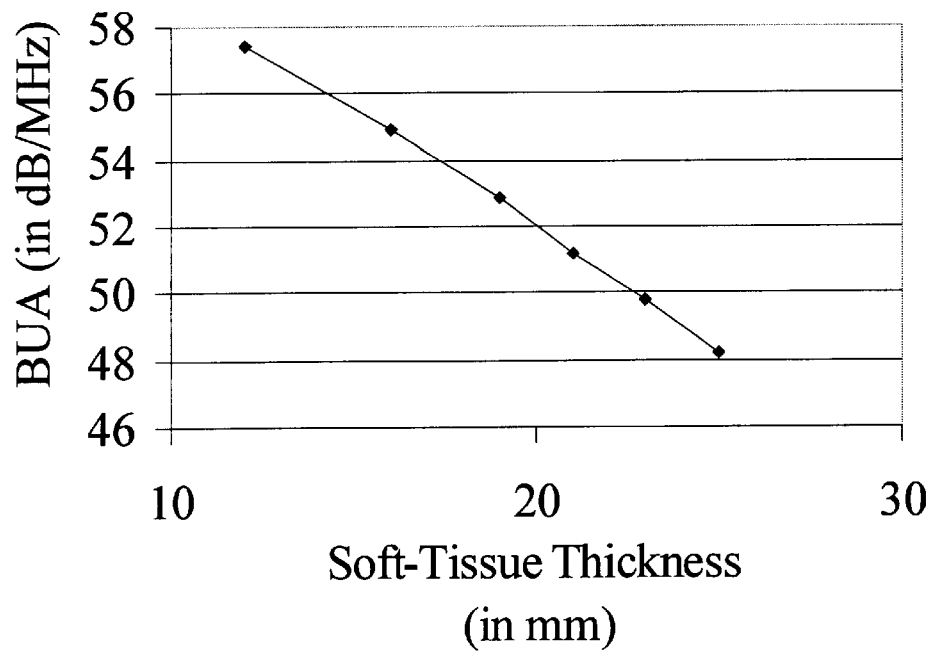
FIG. 4A shows an example demonstrating the influence of soft tissue thickness on measurements of broadband ultrasonic attenuation. As the thickness of the soft tissue interposed in the scan path increases, measured broadband ultrasonic attenuation values, in this example of the calcaneus, decrease.

In this model of soft tissue edema, SOS can decrease by approximately 1–2 percent with increasing soft tissue thickness as is shown in FIG. 3A. BUA values can decrease by approximately 10–20 percent with increasing soft tissue thickness as is shown in FIG. 4A. (Note that actual attenuation of broadband ultrasonic waves increases as soft tissue thickness increases, while BUA values (dB/MHz) decrease as soft tissue thickness increases. This distinction is often not recognized in the literature, which leads to misleading or potentially misleading conclusions about the effect of soft tissue on actual attenuation of broadband ultrasonic waves and BUA values.) While the magnitude of these changes may vary depending on technical factors and injection technique, the model indicates that changes in soft tissue edema can alter SOS and BUA measurements of the calcaneus significantly. When this change in SOS or BUA is related to the reference range of SOS and BUA values in normal volunteers, it can be equivalent to a quarter to one half of a standard deviation. This shows that soft tissue edema adds marked inaccuracy in determining a patient's fracture risk.

Figure 3B:
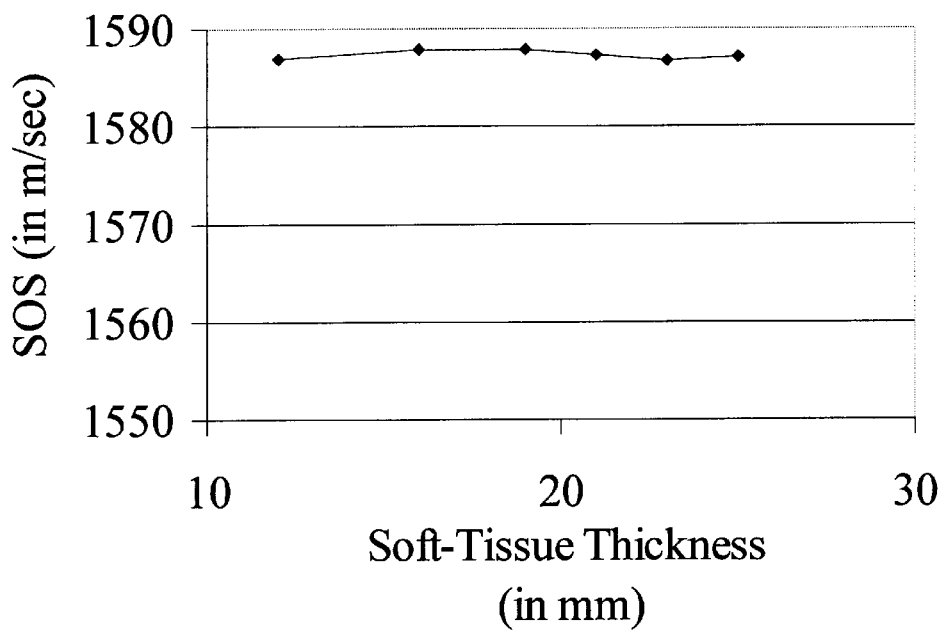
FIG. 3B shows an example demonstrating the results when measured speed of sound is corrected for thickness of the soft tissue layers interposed in the scan path. This correction is typically performed by measuring soft tissue thickness with A-scan or B-scan ultrasonics. As the soft tissue thickness increases, corrected speed of sound does not change significantly.

In some clinical situations, the relationship between soft tissue thickness and induced change in SOS and BUA may be relatively linear as is shown in FIGS. 3A and 4A. The measured value of SOS and BUA that is obtained with the smallest amount of soft tissue edema, i.e. prior to injection of saline, approximates the true SOS and BUA of the calcaneus most closely. If the relationship is linear, a linear correction factor can be used to estimate true calcaneal SOS or BUA based on measured SOS or BUA, ultrasonic measured soft tissue thickness in the edematous state ($D_{edematous}$), and previously measured soft tissue thickness in the non-edematous state ($D_{min}$). Estimated true SOS ($SOS_{true}$) can be defined as:

$$SOS_{true} = SOS_{measured} + [(D_{edematous} - D_{min})/K_{SOS}] \quad [\text{Eq. 1}],$$

where $SOS_{measured}$ is the measured speed of sound, D is the sum of the soft tissue thickness measured on the left side and on the right side of the heel either in the edematous ($D_{edematous}$) or the non-edematous state ($D_{min}$), and $K_{SOS}$ is a correction factor (in sec). Since the relationship between soft tissue thickness and speed of sound is approximately linear in this model, the correction factor $K_{SOS}$ can be calculated as:

$$K_{SOS} = |(D_{max} - D_{min})/(SOS_{measuredDmax} - SOS_{measuredDmin})| \quad [\text{Eq. 2}],$$

where $D_{max}$ is maximum tissue thickness, i.e. tissue thickness with maximum edema, $D_{min}$ is minimum tissue thickness, i.e. tissue thickness in the non-edematous state, $SOS_{measuredDmax}$ is measured speed of sound at maximum tissue thickness and $SOS_{measuredDmin}$ is measured speed of sound at minimum tissue thickness. Using Eq. 2, $K_{SOS}$ equals 0.00037 in the current example shown in FIG. 3A for measurements of speed of sound. Using this correction factor $K_{SOS}$, speed of sound can be corrected for soft tissue thickness as is shown in FIG. 3B. One skilled in the art will readily recognize substitute equations, including those for non-linear relationships, such as exponential, logarithmic, or polynomial functions.

Figure 4B:
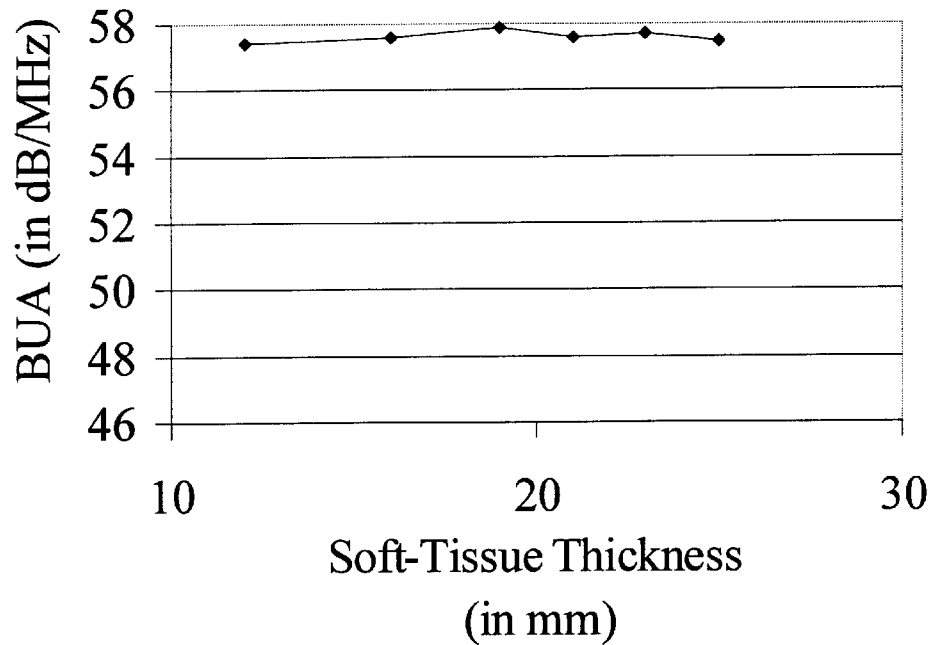
FIG. 4B shows a prophetic example demonstrating the result, when measured broadband ultrasonic attenuation is corrected for thickness of the soft tissue layers interposed in the scan path. This correction is typically performed by measuring soft tissue thickness with A-scan or B-scan ultrasonics. As the soft tissue thickness increases, corrected broadband ultrasonic attenuation values do not change significantly.

Estimated true BUA ($BUA_{true}$) can be defined as:

$$BUA_{true} = BUA_{measured} + [(D_{edematous} - D_{min})/K_{BUA}] \quad [\text{Eq. 3}],$$

where $BUA_{measured}$ is the measured broadband ultrasonic attenuation, D is the sum of the soft tissue thickness measured on the left side and on the right side of the heel either in the edematous ($D_{edematous}$) or the non-edematous state ($D_{min}$) and $K_{BUA}$ is a correction factor (in MHz m /dB ). Since the relationship between soft tissue thickness and broadband ultrasonic attenuation is approximately linear in this model, the correction factor $K_{BUA}$ can be calculated as:

$$K_{BUA} = |(D_{max} - D_{min})/(BUA_{measuredDmax} - BUA_{measuredDmin})| \quad [\text{Eq. 4}],$$

where $D_{max}$ is maximum tissue thickness, e.g. tissue thickness with maximum edema, $D_{min}$ is minimum tissue thickness, e.g. tissue thickness in the non-edematous state, $BUA_{measuredDmax}$ is measured broadband ultrasonic attenuation it maximum tissue thickness and $BUA_{measuredDmin}$ is measured broadband ultrasonic attenuation at minimum tissue thickness. Using Eq. 4, $K_{BUA}$ equals 0.0014 in the current example shown in FIG. 4A for measurements of broadband ultrasonic attenuation. Using this correction factor $K_{BUA}$, broadband ultrasonic attenuation can be corrected for soft tissue thickness as is shown in FIG. 4B. One skilled in the art will readily recognize substitute equations, including those for non-linear relationships, such as exponential, logarithmic, or polynomial functions.

The prophetic data presented in FIGS. 3B and 4B demonstrate that good estimates of true SOS and true BUA in the non-edematous state can be achieved using equations 1–4.

As an alternative to equations 1 and 2, true SOS without influence of soft tissue contributions ($SOS_{true\ without\ soft\ tissue}$) can be calculated using equations 5 and 6, if the relationship between soft tissue thickness and SOS is linear or close to linear:

$$SOS_{true\ without\ soft\ tissue} = SOS_{measured} + F_{SOS} \times D_{SOSmeasured} \quad [\text{Eq. 5}],$$

where $SOS_{measured}$ is the measured speed of sound, $D_{SOSmeasured}$ is the sum of the soft tissue thickness measured on the left side and on the right side of the heel at the time of the speed of sound measurement, and $F_{SOS}$ is a correction factor (in 1/sec). Since the relationship between soft tissue thickness and speed of sound is approximately linear in this model, the correction factor $F_{SOS}$ can be calculated as:

$$F_{SOS} = |(SOS_1 - SOS_2)/(D_1 - D_2)| \quad [\text{Eq. 6}],$$

where $SOS_1$ is speed of sound measured for a given soft tissue thickness $D_1$, and $SOS_2$ is speed of sound measured for a given soft tissue thickness $D_2$.

Using equations 5 and 6 and the data shown in FIG. 3A, true SOS without influence of soft tissue contributions ($SOS_{true\ without\ soft\ tissue}$) can be calculated as follows:

$$\begin{aligned}
F_{SOS} &= |(SOS_1 - SOS_2)/(D_1 - D_2)| \\
&= |(1577\ \text{msec}^{-1} - 1557\ \text{msec}^{-1})/(0.016\ \text{m} - 0.023\ \text{m})| \\
&= |20\ \text{msec}^{-1}/(-0.007\ \text{m})| \\
&= 2857.1\ \text{sec}^{-1}
\end{aligned}$$

$$\begin{aligned}
SOS_{true\ without\ soft\ tissue} &= SOS_{measured} + F_{SOS} \times D_{SOSmeasured} \\
&= 1587\ \text{msec}^{-1} + 2857.1\ \text{sec}^{-1} \times 0.012\ \text{m} \\
&= 1587\ \text{msec}^{-1} + 34.3\ \text{msec}^{-1} \\
&= 1621.3\ \text{msec}^{-1}
\end{aligned}$$

As an alternative to equations 3 and 4, true BUA without influence of soft tissue contributions ($BUA_{true\ without\ soft\ tissue}$) can be calculated using equations 7 and 8, if the relationssship between soft tissue thickness and BUA is linear or close to linear:

$$BUA_{true\ without\ soft\ tissue} = BUA_{measured} + F_{BUA} \times D_{BUAmeasured} \quad [\text{Eq. 7}],$$

where $BUA_{measured}$ is the measured broadband ultrasonic attenuation, $D_{BUAmeasured}$ is the sum of the soft tissue thickness measured on the left side and on the right side of the heel at the time of the broadband ultrasonic attenuation measurement, and $F_{BUA}$ is a correction factor (in dB/MHz m). Since the relationship between soft tissue thickness and broadband ultrasonic attenuation is approximately linear in this model, the correction factor $F_{BUA}$ can be calculated as:

$$F_{BUA} = |(BUA_1 - BUA_2)/(D_1 - D_2)| \quad [\text{Eq. 8}],$$

where $BUA_1$ is broadband ultrasonic attenuation measured for a given soft tissue thickness $D_1$, and $BUA_2$ is broadband ultrasonic attenuation measured for a given soft tissue thickness $D_2$.

Using equations 7 and 8 and the data shown in FIG. 4, true BUA without influence of soft tissue contributions ($BUA_{true\ without\ soft\ tissue}$) can be calculated as follows:

$$F_{BUA} = |(BUA_1 - BUA_2)/(D_1 - D_2)|$$
$$= |(54.9\,dB\ MHz^{-1} - 49.8\,dB\ MHz^{-1})/(0.016\,m - 0.023\,m)|$$
$$= |5.1\,dB\ MHz^{-1}/(-0.007\,m)|$$
$$= 728.6\,dB\ MHz^{-1} m^{-1}$$

$$BUA_{true\ without\ soft\ tissue} = BUA_{measured} + F_{BUA} \times D_{BUAmeasured}$$
$$= 59.5\,dB\ MHz^{-1} +$$
$$728.6\,dB\ MHz^{-1} m^{-1} \times 0.012\,m$$
$$= 59.5\,dB\ MHz^{-1} + 8.74\,dB\ MHz^{-1}$$
$$= 68.2\,dB\ MHz^{-1}$$

One skilled in the art will readily recognize substitute equations for calculating or estimating SOS and BUA, including those for non-linear relationships between soft tissue thickness and SOS or BUA, such as exponential, logarithmic, or polynomial functions.

Example 2
Correction of Tissue Edema Induced Changes in Speed of Sound and Broadband Ultrasonic Attenuation of the Calcaneus using Look-Up Tables This example documents, among other things, how a correction table for speed of sound and broadband ultrasonic attenuation can be developed for various thicknesses of the soft tissue located within the ultrasonic beam path. Such a correction table can be particularly useful in a patient who has abnormally thick soft tissues, such as a patient with peripheral edema secondary to compromised cardiac, renal, hepatic, or vascular function. A correction table of SOS and BUA for soft tissue thickness like the one developed in this Example can be used as an alternative or an improvement to the corrections and derivations of the corrections presented in Example 1, i.e. corrections assuming linear, non-linear, exponential, logarithmic, polynomial, or other functions. One skilled in the art will readily recognize substitute materials and methods to correct speed of sound and broadband ultrasonic attenuation measurements for thickness of the soft tissue interposed in the beam path.

Speed of sound and broadband ultrasonic attenuation measurements are performed in a volunteer, healthy young Caucasian female(s) less than 30 years of age who has an ethically and medically established need for leg amputation. Such a volunteer would typically be subject to an advanced and operable osteosarcoma in the leg. The experimental specimen consists of a foot and calf extending to the knee joint. Skin, subcutaneous tissue, muscle tissue, fascia, bone, and all other tissue in the specimen are intact and have not been damaged by specimen preparation or other extrinsic manipulation. All ultrasonic experiments are performed in the heat chamber at body temperature and immediately post amputation.

Prior to and after amputation, the specimen is subjected to magnetic resonance imaging (MRI) using a 1.5 Tesla whole-body MRI system (Siemens Vision, Siemens Medical Systems, Erlangen, Germany). Before the specimen is placed in the magnet, the site at which ultrasonic speed of sound and broadband ultrasonic attenuation measurements will be performed is marked on the skin on the medial and lateral aspect of the heel using india ink. Vitamin E capsules are then secured to the skin over the medial and lateral india ink skin mark. Vitamin E capsules are secured to the skin using adhesive tape. Vitamin E capsules are easily identified on MR images and mark the ultrasonic beam path on the MR images. The specimen is placed in a knee coil and advanced into the isocenter of the magnet. T1-weighted spin-echo images are obtained with a repetition time TR of 600 msec, an echo time TE of 20 msec, 2 numbers of excitations (NEX), a field of view of 14×14 cm, and a matrix consisting of 256×256 picture elements. Images are obtained in the axial, coronal, and sagittal plane. The two-dimensional MR images are reconstructed using the built in scanner software and are displayed on the scanner viewing console. The axial image that displays the medially and laterally placed Vitamin E capsules marking the ultrasonic beam is selected and the following distances are measured: (a) thickness of the calcaneus in the area of the ultrasonic beam path, (b) medial soft tissue thickness, i.e. sum of subcutaneous fat and muscle medially, (c) lateral soft tissue thickness, i.e. sum of subcutaneous fat and muscle laterally. These MRI distance measurements are performed using calipers provided with the scanner software that are manually placed at the various tissue interfaces. The sum of the thickness of the medial and the lateral soft tissue layer measured by MRI is calculated and is assigned baseline soft tissue thickness ($D_{soft\ tissue\ baseline}$). Such measurements can be correlated with the ultrasonic results obtained herein.

The specimen is removed from the MRI system and submitted to ultrasonic scanning. Ultrasonic interrogation described herein is performed both pre- and post-operatively. Ultrasonic measurements are performed using a prototype ultrasonic system that is capable of two-dimensional image acquisition and display using B-scan technology in addition to SOS and BUA measurements. A small amount of acoustic coupling gel is applied to the skin and the ultrasonic transducers are placed against the skin at the previously marked skin site at the medial and lateral aspect of the heel.

Two-dimensional gray-scale images of the heel are obtained at the measurement site. The distance from the probe/skin interface to the soft tissue/bore interface, i.e. the soft tissue thickness, is measured on the medial and the lateral side of the heel at the measurement site. The sum of the soft tissue thickness measured on the medial and the lateral side of the heel is calculated. SOS and BUA are then measured in the same location. The measured SOS and BUA values are assigned as baseline SOS ($SOS_{baseline}$) and baseline BUA ($BUA_{baseline}$).

Tissue samples composed of skin, subcutaneous fat, and muscle are obtained from the abdominal region of a beef carcass. The hair is removed from all tissue samples prior to cutting. Tissue samples are cut into slices with thicknesses ranging) from 1–30 mm at 1 mm increments. Slices that are thinner than 5 mm are composed only of subcutaneous fat. Slices that are 5 mm and more thick are cut in a fashion so that they contain a muscle layer that does not exceed 3 mm in thickness in addition to skin and subcutaneous fat. Alternatively, after the operation fat tissue may be obtained from the amputated tissue.

The specimen is removed from the ultrasonic system. A 1 mm slice of bovine tissue is placed at the medial aspect of the heel. The specimen along with the slice of bovine tissue secured to the medial measurement site is returned into the ultrasonic device, a small amount of acoustic coupling gel is applied medially and laterally, and (a) speed of sound, (b)

broadband ultrasonic attenuation, and (c) medial and lateral soft tissue thickness are measured. Measured soft tissue thickness consists of both peripheral bovine and underlying human soft tissue. The sum of the soft tissue thickness measured on the medial and the lateral side of the heel is calculated.

The specimen is removed from the ultrasonic system. A 1 mm slice of bovine tissue is placed at the lateral aspect of the heel in addition to the slice previously placed at the medial aspect of the heel. The specimen along with the slices of bovine tissue secured to the medial and lateral measurement site is returned into the ultrasonic device, a small amount of acoustic coupling gel is applied medially and laterally, and (a) speed of sound, (b) broadband ultrasonic attenuation, and (c) medial and lateral soft tissue thickness are measured. Measured soft tissue thickness consists of both peripheral bovine and underlying human soft tissue. The sum of the soft tissue thickness measured on the medial and the lateral side of the heel is calculated.

The experiment is repeated in a step-wise fashion while increasing first the medial and then the lateral soft tissue thickness, each in 1 mm increments, by using thicker slices of bovine tissue up to a maximum of 30 mm of medial bovine slice thickness and 30 mm of lateral bovine slice thickness.

As the thickness of the soft tissue layers interposed in the ultrasonic beam path increases, speed of sound and broadband ultrasonic attenuation values decrease continuously. However, since baseline speed of sound and baseline broadband ultrasonic attenuation prior to increasing soft tissue thickness above normal levels are known, correction factors for speed of sound and broadband ultrasonic attenuation can be calculated for individual soft tissue thicknesses similar to the methods presented in Example 1. Such correction factors can be stored in a "look-up table". Alternatively, such values may be obtained using the type of measurements in Example 1. Such look-up tables can be used in human subjects to correct speed of sound or broadband ultrasonic attenuation measurements of the calcaneus for the thickness of the overlying soft tissue layer. Such look-up tables are particularly useful for patients with compromised cardiac, renal, hepatic, or vascular function with peripheral edema. Such look-up tables can be used in such patients to (a) correct for pathologic increases in soft tissue thickness resulting from tissue edema and to (b) correct for variations in the amount of edema and associated soft tissue thickness which can be seen with worsening of the patient's underlying medical condition or improvement of the patient's underlying medical condition, for example due to medical intervention. Such look-up tables can also be used to correct for diurnal changes, e.g. small amount of peripheral edema and associated soft tissue thickness in the morning and large amount of peripheral edema and associated soft tissue thickness in the evening.

Since soft tissue swelling can be asymmetrical, i.e. affect one side, medial or lateral, more than the other side, the experiment is repeated, with the slices of bovine tissue only applied to the medial side of the heel. In this model of asymmetrical, unilateral medial soft tissue edema, the experiment is repeated in a step-wise fashion while increasing the thickness of the medial soft tissue layer in 1 mm increments from 1 mm up to a maximum of 30 mm. The same experiment is then repeated with the slices of bovine tissue only applied to the lateral side of the heel while increasing the thickness of the lateral soft tissue layer in 1 mm increments from 1 mm up to a maximum of 30 mm.

As the thickness of the soft tissue layers interposed in the ultrasonic beam path increases, speed of sound and broadband ultrasonic attenuation decrease continuously. However, since baseline speed of sound and baseline broadband ultrasonic attenuation prior to increasing soft tissue thickness above normal levels are known, correction factors for speed of sound and broadband ultrasonic attenuation can be calculated for individual soft tissue thicknesses in this model of asymmetrical edema similar to the methods presented in Example 1. Such correction factors for asymmetrical medial or lateral soft tissue edema can be stored in a "look-up table". Such look-up tables can be used in human subjects to correct speed of sound or broadband ultrasonic attenuation measurements of the calcaneus for the thickness of the overlying sort tissue layer in asymmetrical edema. Such look-up tables are particularly useful for patients with compromised cardiac, renal, hepatic, or vascular function and asymmetrical peripheral edema.

In another series of experiments, all overlying soft tissues are surgically removed from the specimen's heel and the bony surface of the calcaneus is exposed. Speed of sound and broadband ultrasonic attenuation measurements of the calcaneus are repeated over the same measurement site used in the previous experiments. Thus, true speed of sound ($SOS_{true}$) and true broadband ultrasonic attenuation ($BUA_{true}$) of the calcaneus are determined unaffected by any, not even normal, overlying soft tissues. The SOS and BUA measurements described above for bilateral symmetrical, unilateral asymmetrical medial, and unilateral asymmetrical lateral edema are repeated using the previously prepared slices of bovine tissue.

As the thickness of the soft tissue layers interposed in the ultrasonic beam path increases, speed of sound and broadband ultrasonic attenuation values decrease continuously. However, since true speed of sound and true broadband ultrasonic attenuation prior to increasing soft tissue thickness are known, correction factors for speed of sound and broadband ultrasonic attenuation can be calculated for individual soft tissue thicknesses similar to the methods presented herein. Example 1. Such correction factors can be stored in a "look-up table". Such look-up tables can be used in human subjects to correct measured speed of sound or measured broadband ultrasonic attenuation of the calcaneus for the presence and thickness of any normal or pathologically enlarged overlying soft tissue layer. Such look-up tables provide an estimate of true speed sound and true broadband ultrasonic attenuation independent of overlying soft tissue thickness. Such corrections are particularly useful for comparing different individuals and populations, since SOS and BUA measurements corrected in this fashion will not be affected by normal variations in soft tissue thickness or pathologic increases in soft tissue thickness, e.g. in the presence of tissue edema.

Example 3

Correction of Tissue Edema Induced Changes in Speed of Sound of the Calcaneus using Previously Published Data on SOS in Various Soft Tissues This example documents, among other things, how speed of sound can be corrected for variations in thickness of the soft tissue located within the ultrasonic beam path by measuring the thickness of the interposed soft tissue layers using A-scan or B-scan technology and by eliminating soft tissue induced changes in measured SOS of the calcaneus using previously known and published data for soft tissue SOS. Such corrections are particularly useful in patients who have abnormally thick soft tissues such as patients with peripheral edema secondary to compromised cardiac, renal, hepatic, or vascular function. Corrections of measured SOS for soft tissue thickness like the one developed in this example can be used as an alternative or an improvement to the corrections and derivations of the corrections presented in Examples 1 and 2, i.e. corrections assuming linear, non-linear, exponential, logarithmic or other functions. One skilled in the art will readily recognize substitute materials and methods to correct speed of sound and broadband ultrasonic attenuation measurements for thickness of the soft tissue interposed in the beam path.

Five patients with compromised cardiac function and peripheral edema are selected. A trained physician examines all five patients clinically for visual or palpatory evidence of edema in the morning before 10 am and in the evening after 5 pm. Edema is clinically evaluated anterior to the tibia by visual inspection and manual palpation. Using standard clinical techniques (see Bates et al., J. B. Lippincott, 1995), edema is subdivided into 5 grades:

0.) absent,
1.) slight,
2.) mild,
3.) moderate, and
4.) severe.

Ultrasonic measurements are performed in each patient in the morning before 10 am and in the evening after 5 pm shortly after the clinical examination using a prototype ultrasonic system that is capable of two-dimensional image acquisition and display using B-scan technology in addition to SOS and BUA measurements. The patient's foot is secured in the ultrasonic device so that the heel of the foot rests on the heel pad of the device and the posterior aspect of the heel touches the back-wall of the instrument (see also FIG. 5C). The measurement site is marked on the skin with india ink on the left and right side of the heel. A small amount of acoustic coupling gel is applied to the skin and the ultrasonic transducers are placed against the skin at the measurement site.

Two-dimensional gray-scale images of the heel are obtained at the measurement site. The distance from the probe/skin interface to the soft tissue/bore interface, i.e. the soft tissue thickness, is measured on the left and the right side of the heel at the measurement site. The sum of the soft tissue thickness measured on the left and the right side of the heel ($D_{soft\ tissue}$) is calculated. SOS and BUA are then determined in the same location.

For determining SOS, the instrument measures initially the total travel time of the ultrasonic beam through the calcaneus and the medial and lateral soft tissue ($T_{total}$). Since the device registers the physical distance between the medial and the lateral transducer and since both are in contact with the skin medially or laterally, the total thickness of the heel ($D_{heel}$) is known. Global speed of sound for combined bone and soft tissue components is thus calculated as:

$$SOS_{Global} = D_{heel}/T_{total} \qquad [Eq.\ 9]$$

This measurement and calculation is widely used in most current ultrasonic instruments used for measuring calcaneal speed of sound. However, it is evident that not only bone, but also soft tissue components contribute to the total travel time which explains why calcaneal SOS is artifactually lowered in the presence of soft tissue swelling.

Using equations 10–16 described below, true calcaneal SOS without alterations resulting from soft tissue layers interposed in the ultrasonic beam path can be calculated. Total travel time through bone and soft tissues ($T_{total}$) can also be described as:

$$T_{total} = T_{calcaneus} + T_{soft\ tissue} \qquad [Eq.\ 10],$$

where $T_{calcaneus}$ is the travel time of the ultrasonic beam through the calcaneus and $T_{soft\ tissue}$ is the travel time of the ultrasonic beam through the soft tissues medial and lateral of the calcaneus. Thus, $T_{calcaneus}$ is defined as:

$$T_{calcaneus} = T_{total} - T_{soft\ tissue} \qquad [Eq.\ 11]$$

$T_{soft\ tissue}$ is defined as:

$$T_{soft\ tissue} = D_{soft\ tissue}/SOS_{soft\ tissue} \qquad [Eq.\ 12]$$

$D_{soft\ tissue}$ is measured using A-scan or B-scan technology (see also Examples-General Materials and Methods) and represents the sum of soft tissue thickness medial and lateral to the calcaneus. $SOS_{soft\ tissue}$ is known for different soft tissues from the literature (see Goss et al., J. Acoust. Soc. Am., 1978). For example, speed of sound of human fat tissue has been reported to be 1479 m/sec at 37° Celsius (sec Goss et al., J. Acoust. Soc. Am., 1978). Thus, $T_{soft\ tissue}$ can be calculated by measuring $D_{soft\ tissue}$ using A-scan or B-scan technology and by using previously published data for $SOS_{soft\ tissue}$. Since $T_{total}$ has been measured and $T_{soft\ tissue}$ has been calculated using Eq. 12, $T_{calcaneus}$ can be determined using Eq. 11.

The thickness of the calcaneus ($D_{calcaneus}$) can be determined using the following equation:

$$D_{calcaneus} = D_{heel} - D_{soft\ tissue} \qquad [Eq.\ 13].$$

Thus, true calcaneal speed of sound without any soft tissue interference is defined as:

$$SOS_{calcaneus} = D_{calcaneus}/T_{calcaneus} \qquad [Eq.\ 14],$$

or $$SOS_{calcaneus} = D_{heel} - D_{soft\ tissue}/T_{total} - T_{soft\ tissue} \qquad [Eq.\ 15],$$

or $$SOS_{calcaneus} = D_{heel} - D_{soft\ tissue}/(T_{total} - D_{soft\ tissue}/SOS_{soft\ tissue}) \qquad [Eq.\ 16].$$

Clinical examination in all 5 patients will typically show that peripheral edema has increased by the evening when compared to morning. Global speed of sound for combined bone and soft tissue components will be typically decreased in all 5 patients in the evening when compared to the morning measurement because of the increase in tissue edema and associated soft tissue swelling. Thus, global speed of sound measurements are subject to diurnal changes dependent on the amount of edema and soft tissue swelling present. True calcaneal speed of sound calculated as described in Eq. 10–16, however, shows only mild variation for each patient between morning and evening measurements indicating that this parameter is less dependent on tissue edema and provides a more accurate description of bone mineral density and structure of the calcaneus.

Example 4

Correlation of Speed of Sound and Broadband Ultrasonic Attenuation of the Calcaneus with Calcaneal Bone Mineral Density Measurements Assessed by Dual X-Ray Absorptiometry in Patients with Peripheral Edema before and after Correction for Soft Tissue Thickness This example documents, among other things, that correlations between speed of sound or broadband ultrasonic attenuation and bone mineral density (BMD) of the calcaneus measured by dual x-ray absorpiometry (DXA) deteriorate in the presence of soft tissue edema in patients with compromised cardiac function, compromised renal function, compromised hepatic function, or compromised vascular function. This example documents also that correlations between speed of sound or broadband ultrasonic attenuation and BMD of the calcaneus measured by DXA improve when SOS and BUA measurements are corrected for the thickness of the soft tissue that overlies the calcaneus in the ultrasonic beam path.

Twenty patients with compromised cardiac function and peripheral edema are studied with speed of sound and broadband ultrasonic attenuation measurements of the calcaneus and with bone mineral density measurements of the axial and peripheral skeleton using dual x-ray absorptiometry.

Ultrasonic measurements are performed in each patient using a prototype ultrasonic system that is capable of two-dimensional image acquisition and display using B-scan technology in addition to SOS and BUA measurements. The patient's foot is secured in the ultrasonic device so that the heel of the foot rests on the heel pad of the device and the posterior aspect of the heel touches the back-wall of the instrument (see also FIG. 5C). The measurement site is marked on the skin with india ink on the left and right side of the heel. A small amount of acoustic coupling gel is applied to the skin and the ultrasonic transducers are placed against the skin at the measurement site.

Two-dimensional gray-scale images of the heel are obtained at the measurement site. The distance from the probe/skin interface to the soft tissue/bone interface, i.e. the soft tissue thickness, is measured on the left and the right side of the heel at the measurement site. The sum of the soft tissue thickness measured on the left and the right side of the heel ($D_{soft\ tissue}$) is calculated. SOS and BUA are then measured in the same location.

Dual x-ray absorptiometry (DXA) is performed using a lunar Expert DXA system (Lunar Corporation, 313 West Beltline Hwy., Madison, Wis. 53713). In each patient, DXA measurements are performed in the following anatomic regions:

In the lumbar spine in AP projection extending from lumbar vertebral level 1 to lumbar vertebral level 4.

In the lumbar spine in lateral projection extending from lumbar vertebral level 2 to lumbar vertebral level 4 or the next higher lumbar vertebral level that is not superimposed by the iliac crest in the lateral projection; L2 is excluded from the analysis in those patients in whom ribs are superimposed on this vertebral body.

In the hip, measuring the intertrochanteric region and the region called "Ward's triangle".

In the distal radius.

In the calcaneus.

DXA measurements in the calcaneus are performed in the same region that is evaluated with speed of sound and broadband ultrasonic attenuation measurements. Bone mineral density (BMD) measurements in these anatomic regions are expressed as $mg/cm^2$.

Correlations between DXA and SOS and BUA improve when soft tissue thickness is measured ultrasonographically and SOS and BUA are corrected for soft tissue thickness using the methods and devices described in Examples 2 and 3.

Example 5

Correction for Edema-Induced Changes in Ultrasonic Probe Position and Its Influence on In-Vivo Reproducibility of Calcaneal Speed of Sound and Broadband Ultrasonic Attenuation This example shows among other things that presence of peripheral edema does not only affect soft tissue thickness in the beam path thereby altering SOS and BUA directly (see Examples 1–4), but also affects ultrasonic probe position relative to the underlying bone. This examples documents that edema induced changes in ultrasonic probe position over the calcaneus and general variations in ultrasonic probe position over the calcaneus reduce short-term and long-term in vivo precision of SOS and BUA measurements.

Twenty patients with compromised cardiac performance and peripheral edema are selected for the study. SOS and BUA measurements are performed at different times in the day on two different days: In the morning on day 1 before 9 am and in the evening on day 2 after 6 pm. At each time interval, the degree of peripheral edema is assessed clinically by visual inspection and manual palpation. Using standard clinical techniques (see Bates et al., J. B. Lippincott. 1995), edema is subdivided into 5 grades:

0.) absent,

1.) slight,

2.) mild,

3.) moderate, and

4.) severe.

Ultrasonic measurements are performed in each patient using a first prototype ultrasonic system that is capable of two-dimensional image acquisition and display using B-scan technology in addition to SOS and BUA measurements. The patient's foot is secured in the ultrasonic device so that the heel of the foot rests on the heel pad of the device and the posterior aspect of the heel touches the back-wall of the instrument (see also FIGS. 5A and 5B). A small amount of acoustic coupling gel is applied to the skin and the ultrasonic transducers are placed against the skin at the measurement site.

Two-dimensional B-mode gray-scale images of the heel are obtained at the measurement site using this first prototype system. The distance from the probe/skin interface to the soft tissue/bone interface, i.e. the soft tissue thickness, is measured on the left and the right side of the heel at the measurement site. The sum of the soft tissue thickness measured on the left and the right side of the heel ($D_{soft\ tissue}$) is calculated. SOS and BUA are then measured in the same location yielding $SOS_{measured}$ and $BUA_{measured}$. Measured SOS and BUA are then corrected for soft tissue thickness using methods and techniques similar to those described in Examples 2 and 3 thereby yielding $SOS_{corrected}$ and $BUA_{corrected}$. The prototype ultrasonic system used for this part of the experiment does, however, not correct for changes in the thickness of the inferior and posterior heel pad secondary to edema.

SOS and BUA measurements are then repeated using a second, different prototype ultrasonic system. This second system is capable of identifying the posterior contour and the inferior contour of the calcaneus on the B-scan images. Using these landmarks, the system positions the ultrasonic transducers automatically over a predefined region in the calcaneus, e.g. 1.5 cm anterior to the posterior calcaneal cortex and 1.5 cm superior to the inferior calcaneal cortex. In this fashion, the ultrasonic transducers are reproducibly positioned over the same measurement site in the calcaneus regardless of changes in the thickness of the posterior and inferior heel soft tissue pad (see also FIG. 5C and 5D).

Two-dimensional B-mode gray-scale images of the heel are then obtained at the measurement site using the second prototype ultrasonic system. The distance from the probe/skin interface to the soft tissue/bone interface, i.e. the soft tissue thickness, is measured on the left and the right side of the heel at the measurement site. The sum of the soft tissue thickness measured on the left and the right side of the heel ($D_{soft\ tissue}$) is calculated. SOS and BUA are then measured in the same location yielding $SOS_{measured}$ and $BUA_{measured}$. Measured SOS and BUA are then corrected for soft tissue thickness using methods and techniques similar to those described in Examples, 2 and 3 thereby yielding $SOS_{corrected}$ and $BUA_{corrected}$.

In-vivo reproducibility between am and pm measurements is better with the second ultrasonic system that adjusts probe position relative to the posterior and the inferior cortex of the calcaneus than with the first prototype system with fixed probe position relative to skin/patient/heel surface. In-vivo reproducibility is best when (a) probe position is adjusted relative to the bony landmarks of the calcaneus, e.g. posterior and inferior cortex of the calcaneus, and (b) $SOS_{measured}$ and $BUA_{measured}$ are corrected for medial and lateral soft tissue thickness thereby yielding $SOS_{corrected}$ and $BUA_{corrected}$ (see also Examples 2 and 3).

Example 6
Correction for Edema-Induced Changes in Ultrasonic Probe Position and Its Influence on In-Vivo Reproducibility of Calcaneal Speed of Sound and Broadband Ultrasonic Attenuation before and after Diuretic Therapy The experimental design used in this example is identical to that shown in Example 5. However, rather than assessing the influence of diurnal changes in tissue edema between morning and evening measurements, twenty patients with compromised cardiac performance and peripheral edema are studied prior to and two weeks after initiation of diuretic therapy.

The results show that in-vivo reproducibility of SOS and BUA is better when the ultrasonic system is capable of adjusting probe position relative to the anatomic landmarks, e.g. posterior and inferior cortex, of the calcaneus than with an ultrasonic system where the probe position is fixed relative to skin/patient/heel surface. In-vivo reproducibility is best when (a) probe position is adjusted relative to the bony landmarks of the calcaneus, e.g. posterior and inferior cortex of the calcaneus, and (b) $SOS_{measured}$ and $BUA_{measured}$ are corrected for medial and lateral soft tissue thickness thereby yielding $SOS_{corrected}$ and $BUA_{corrected}$ (see also Examples 2 and 3).

Publications
U.S. Patent Documents

| | | |
|---|---|---|
| 3,648,685 | Mar. 14, 1972 | Hepp, J. A., et al. |
| 3,713,329 | Jan. 30, 1973 | Munger, D. W. |
| 3,782,177 | Jan. 1, 1974 | Hoop, J. M. |
| 3,847,141 | Nov. 12, 1974 | Hoop, J. M. |
| 4,043,181 | Aug.23, 1977 | Nigam, A. K. |
| 4,048,986 | Sep. 20, 1977 | Ott, J. H. |
| 4,056,970 | Nov. 8, 1977 | Sollish, B. D. |
| 4,224,829 | Sep. 30, 1980 | Kawabuchi, M., et al. |
| 4,235,243 | Nov. 25, 1980 | Saha, S. |
| 4,242,911 | Jan. 6, 1981 | Martin, H. E. |
| 4,361,154 | Nov. 30, 1982 | Pratt, G. W. |
| 4,421,119 | Dec. 20, 1983 | Pratt, G. W. |
| 4,446,737 | May 8, 1984 | Hottier, F. |
| 4,522,068 | Jun. 11, 1985 | Smith, G. E. |
| 4,530,360 | Jul. 23, 1985 | Duarte, L. R. |
| 4,658,827 | Dec. 21, 1987 | He, P., et al. |
| 4,688,428 | Aug. 25, 1987 | Nicolas, J. M. |
| 4,702,258 | Oct. 27, 1987 | Nicolas, J. M., et al. |
| 4,774,959 | Oct. 4, 1988 | Palmer, S. B., et al. |
| 4,830,015 | May 16, 1989 | Okazaki, K. |
| 4,913,157 | Apr. 3, 1990 | Pratt, G. W., et al. |
| 4,930,511 | Jun. 5, 1990 | Rossman, P. J., et al. |
| 5,042,489 | Aug. 27, 1991 | Wiener, S. A., et al. |
| 5,054,490 | Oct. 8, 1991 | Rossman, P. J., et al. |
| 5,099,849 | Mar. 31, 1992 | Rossman, P. J., et al. |
| 5,119,820 | Jun. 9, 1992 | Rossman, P. J., et al. |
| 5,218,963 | Jun. 15, 1993 | Mazess, R. B. |
| 5,271,403 | Dec. 21, 1993 | Paulos, J. J. |
| 5,343,863 | Sep. 6, 1994 | Wiener, S. A., et al. |
| 5,349,959 | Sep. 27, 1994 | Wiener, S. A., et al. |
| 5,452,722 | Sep. 26, 1995 | Langton, C. M. |
| 5,483,965 | Jan. 16, 1996 | Wiener, S. A., et al. |
| 5,603,325 | Feb. 18, 1997 | Mazess, R. B., et al. |
| 5,649,538 | Jul. 22, 1997 | Langton, C. M. |

Foreign Patent Documents
WO 80/02796 Jun. 9, 1980 Pratt, G.
Other Publications
Agren, M., et al., Calc Tiss Int, vol. 48, pp. 240–244, 1991.
Bates, B., et al., in: "A guide to physical examination and history taking, 6th edition", Bates, B., et al., eds., pp. 427–447, 1995.
Biot, M. A., J Acoust Soc Am, vol. 34, pp. 1254–1264, 1962.
Bradenburger, G., et al., J Bone Miner Res, vol. suppl. 1, pp. S184, 1992.
Dretakis, E., et al., Br J Radiol, vol. 67, pp. 636–638, 1994.
Faulkner, K. G., et al., Am J Roentgenol, vol. 157, pp. 1229–37, 1991.
Gluer. C. C., et al., J Bone Min Res, vol. 7 (9), pp. 1071–1079, 1992.
Gluer, C. C., et al., Calc Tiss Int. vol. 55, pp. 46–52, 1994.
Goss, S. A., et al., J Acoust Soc Am, vol. 64 (2), pp. 423–457, 1978.
Greespan, M., et al., J Acoust Soc Am, vol. 31, pp. 75–76, 1959.
Hans, D., et al., Bone, vol. 16, pp. 476–480, 1995.
Lang, P., et al., Radiol Clin North Am. vol. 29. pp. 49–76, 1991.
Langton, C. M., et al., Bone, vol. 18, 6, pp. 495–503, 1996.
Langton, C. M., et al., Eng Med, vol. 13, pp. 89–91, 1984.
McCloskey, E. V., et al., Clin Sci, vol. 78, pp. 221–227, 1990.
Njeh, C. F., et al., Med Eng Phys, vol. 18, pp. 373–381, 1996.
Rossman, P. J., et al., Clin Phys Physiol Meas, vol. 10, pp.353–360, 1989.
Schott, A. M., et al., Osteoporosis Int, vol. 3, pp. 249–254, 1993.
Turner, C. H., et al., Calc Tiss Int, vol. 49, pp. 116–119, 1991.
Williams, J. L., J Acoust Soc Am, vol. 91, pp. 1106–1112, 1992.
Williams, P., et al. "Gray's anatomy, 36th British Edition", 1980.
Zagzebski, J. A., et al., Calc Tiss Int. vol. 49, pp. 107–111, 1991.

All documents and publications, including patents and patent application documents, are herein incorporated by reference to the same extent as if each publication were individually incorporated by reference.

We claim:

1. An ultrasonic system for tissue ultrasonic interrogation, comprising:

a) a first ultrasonic transducer with an axis of transmission in common with a second ultrasonic transducer, said axis of transmission is through a portion of tissue, b) an x, y positioner that engages said first ultrasonic transducer and said second ultrasonic transducer, said x, y positioner controllably positions said first ultrasonic transducer and said second ultrasonic transducer in a desired manner between at least a first and a second position and is adapted to maintain one or more axes of transmission, and c) a z positioner that positions at least said first ultrasonic transducer, and said z positioner changes the distance of transmission along said one or more axes of transmission between said first ultrasonic transducer and said second ultrasonic transducer, and d) at least one computational unit designed to manage ultrasonic signal transmission and reception of said first ultrasonic transducer and said second ultrasonic transducer in either A scan or B scan mode or both and is designed to control movement of said x, y positioner and said z positioner.

2. The ultrasonic system of claim 1, further comprising a second x, y positioner that positions third ultrasonic transducers controlled by said at least one computational unit.

3. The ultrasonic system of claim 1, wherein said at least one computational unit is adapted to estimate broadband ultrasonic attenuation in an interrogated tissue and said computational unit is adapted to correct said broadband ultrasonic attenuation for soft tissue broadband ultrasonic attenuation.

4. The ultrasonic system of claim 3, wherein said at least one computational unit comprises a database of correction factors for soft tissue thicknesses and broadband ultrasonic attenuation.

5. The ultrasonic system of claim 4, wherein said database is comprised of factors related to empirical measurements of soft tissue and broadband ultrasonic attenuation or speed of sound.

6. The ultrasonic system of claim 1, further comprising a second z positioner to position said second ultrasonic transducer.

7. The ultrasonic system of claim 1, wherein said x, y positioner comprises a frame to maintain said axis of transmission between said first and second ultrasonic transducers said frame engages an x track and said x track engages a y track, thereby said first and second ultrasonic transducers can move in either an x or y dimension or combination thereof with respect to an anatomical region.

8. The ultrasonic system of claim 1, wherein said x, y positioner can accommodate an appendage and said appendage is held in a predetermined position in said ultrasonic system relative to said x, y positioner.

9. The ultrasonic system of claim 1, wherein said x, y positioner is remote controlled by said at least one computational unit.

10. The ultrasonic system of claim 1, wherein said at least one computational unit comprises a computational program to identify an anatomic landmark based on either A scan or B scan interrogation or both.

11. The ultrasonic system of claim 10, wherein said at least one computational unit is designed to instruct said x, y positioner to position said first ultrasonic transducer and said second ultrasonic transducer to interrogate said tissue with respect to said anatomic landmark and said x, y positioner generally maintains said axis of transmission between said first ultrasonic transducer and said second ultrasonic transducer at a preselected set of coordiniates in relation to said anatomic landmark.

12. The ultrasonic system of claim 1, wherein said at least one computational unit instructs an x servo-motor to drive said first ultrasonic transducer and second transducer in the x dimension and a y servo-motor to drive said first ultrasonic transducer and second transducer in the y dimension.

13. The ultrasonic system of claim 11, wherein said anatomic landmark is part of an anatomical region selected from the group consisting of a knee, an ankle, and tibia, and further wherein said x, y positioner is adapted to accommodate said anatomical region and said first ultrasonic transducer and said second ultrasonic transducer are adapted for interrogation using broadband ultrasonic attenuation of dense tissue comprising bone.

14. The ultrasonic system of claim 1, wherein said computational unit can identify an anatomic landmark in an interrogated tissue and direct said x, y positioner to a position over said anatomic landmark, thereby said first ultrasonic transducer and second ultrasonic transducer have an axis of transmission generally through said anatomic landmark.

15. An ultrasonic system for tissue ultrasonic interrogation for broadband ultrasonic attenuation or speed of sound measurements, comprising:

a) a first ultrasonic transducer with a first axis of transmission through a first anatomical region to be interrogated and said first ultrasonic transducer is adapted for longitudinal transmission, b) a second ultrasonic transducer with a second axis of transmission through a second anatomical region to be interrogated and adapted for longitudinal reception, wherein said first anatomical region and said second anatomical region permit monitoring broadband ultrasonic attenuation or speed of sound measurements between said first ultrasonic transducer and said second ultrasonic transducer, c) a positioning unit to position said first ultrasonic transducer with respect to said first anatomical region and to position said second ultrasonic transducer with respect to said second anatomical region, d) a z positioner to position at least said first ultrasonic transducer or said second ultrasonic transducer, and e) a computational unit designed to manage ultrasonic signal transmission of said first ultrasonic transducer, to manage ultrasonic signal reception of said second ultrasonic transducer and to control said positioning unit and said z positioner.

16. The ultrasonic system of claim 15, wherein said positioning unit comprises an x, y positioner for said first ultrasonic transducer and said second ultrasonic transducer.

17. The ultrasonic system of claim 15, wherein said x, y positioner is designed to position said first ultrasonic transducer and said second ultrasonic transducer, wherein said first axis of transmission generally has the same axis of transmission as said second axis of transmission.

18. The ultrasonic system of claim 16, wherein said computational unit comprises a program to generate an anatomic landmark to assist in reproducible positioning of said first ultrasonic transducer.

19. An ultrasonic system for ultrasonic interrogation an anatomical region, comprising:

a) a first ultrasonic probe with a first axis of transmission through a tissue, b) a second ultrasonic probe a second axis of transmission through said tissue, c) a first x, y positioner that engages said first ultrasonic probe and said x, y positioner controllably positions said first ultrasonic probe in a desired manner, d) a second x, y positioner that engages said second ultrasonic probe and said x, y positioner controllably positions said second ultrasonic probe in a desired manner, e) a first z positioner that positions at least said first ultrasonic probe, and said z positioner changes the distance of transmission between said first ultrasonic probe and said second ultrasonic probe, and f) at least one computational unit designed to manage ultrasonic signal transmission and reception of said first ultrasonic probe, said second ultrasonic probe and said third ultrasonic probe in either A scan or B scan mode or both and is designed to control movement of at least one said x, y positioner and said z positioner.

20. The ultrasonic system of claim 19, further comprising a second z positioner that positions said second ultrasonic transducer and is controlled by said at least one computational unit.

21. The ultrasonic system of claim 19, further comprising a third x, y positioner that engages a third ultrasonic probe and said third x, y positioner controllably positions said third ultrasonic probe in a desired manner controlled by said at least one computational unit.

22. The ultrasonic system of claim 20, wherein said first x,y positioner, said first z positioner and said first ultrasonic probe are adapted to maintain one or more transmission angles.

23. The ultrasonic system of claim 22, wherein said second x, y positioner, said second z positioner and said second ultrasonic probe are adapted to maintain one or more transmission angles.

24. The ultrasonic system of claim 19, wherein said first ultrasonic probe and said second ultrasonic probe are instructed by said at least one computational unit to controllably vary transmission angles of said first ultrasonic probe said second ultrasonic probe to generate an anatomic map.

25. The ultrasonic system of claim 19, wherein said first ultrasonic probe and said second ultrasonic probe receive signals form each other.

* * * * *